Figure 1:
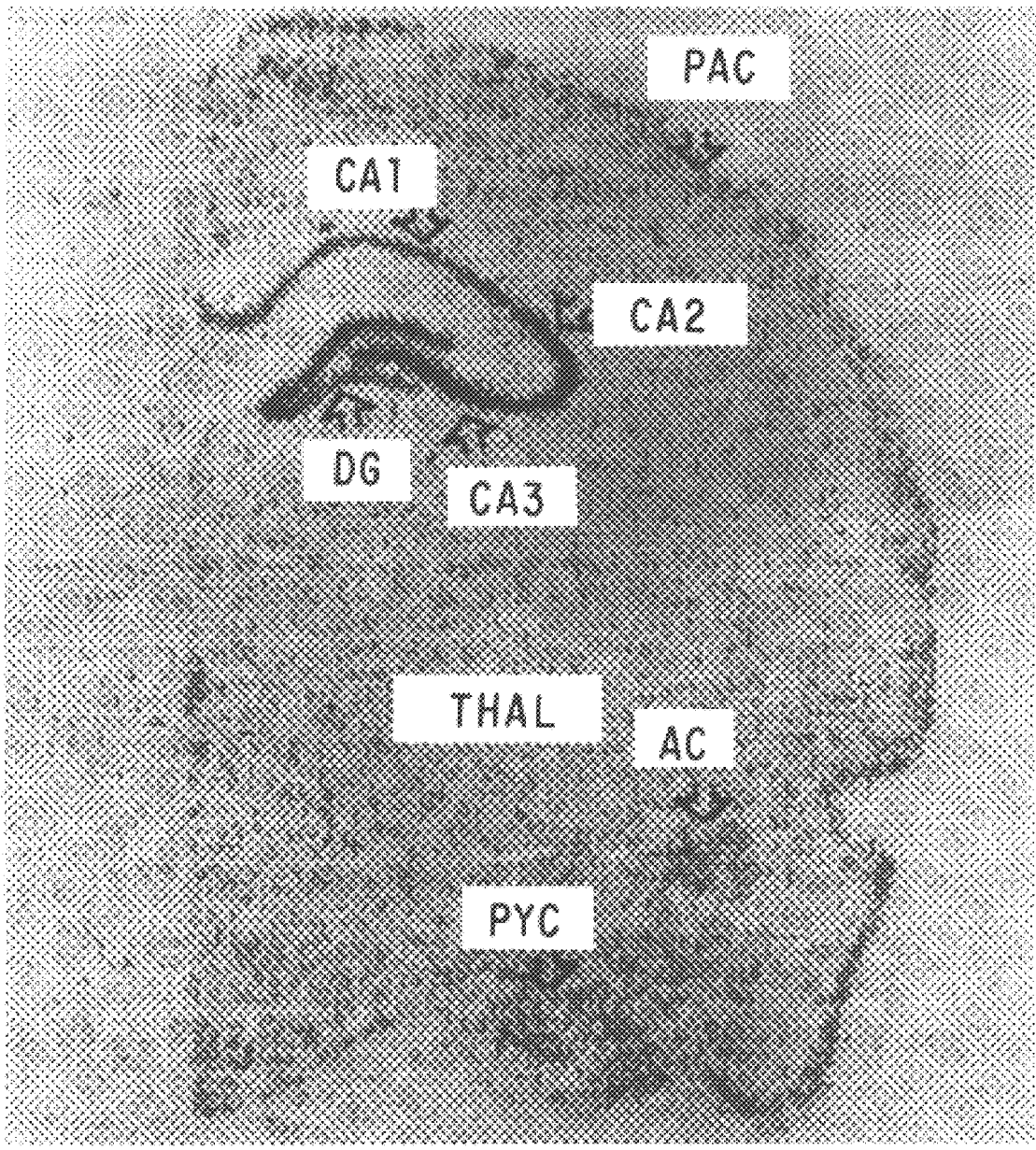

United States Patent [19]

Pasinetti et al.

[11] Patent Number: 5,985,930
[45] Date of Patent: Nov. 16, 1999

[54] TREATMENT OF NEURODEGENERATIVE CONDITIONS WITH NIMESULIDE

[76] Inventors: Giulio M. Pasinetti, 134 E. 93$^{rd}$St., New York, N.Y. 10028; Paul S. Aisen, 26 Broadmoor Rd., Scarsdale, N.Y. 10583

[21] Appl. No.: 08/831,402

[22] Filed: Apr. 1, 1997

Related U.S. Application Data

[60] Provisional application No. 60/033,332, Nov. 21, 1996.

[51] Int. Cl.$^6$ .................................................. A61K 31/16
[52] U.S. Cl. ............................................................ 514/607
[58] Field of Search ............................................. 514/607

[56] References Cited

U.S. PATENT DOCUMENTS

| | | | |
|---|---|---|---|
| 5,486,534 | 1/1996 | Lee et al. | 514/406 |
| 5,510,361 | 4/1996 | Scherz et al. | 514/378 |
| 5,510,368 | 4/1996 | Lau et al. | 514/419 |
| 5,545,656 | 8/1996 | Loose et al. | 514/414 |
| 5,547,975 | 8/1996 | Talley et al. | 514/406 |
| 5,604,260 | 2/1997 | Guay et al. | 514/605 |

FOREIGN PATENT DOCUMENTS

| | | |
|---|---|---|
| 2164559 | 6/1996 | Canada . |
| 002356 | 11/1996 | Italy . |
| WO9413635 | 6/1994 | WIPO . |
| 9414977 | 7/1994 | WIPO . |
| 9500501 | 1/1995 | WIPO . |
| WO9603396 | 2/1996 | WIPO . |
| WO9607651 | 3/1996 | WIPO . |
| WO9608482 | 3/1996 | WIPO . |
| 9611676 | 4/1996 | WIPO . |
| WO9616934 | 6/1996 | WIPO . |
| WO9619469 | 6/1996 | WIPO . |
| WO9623786 | 8/1996 | WIPO . |
| WO9625405 | 8/1996 | WIPO . |
| 9820864 | 5/1998 | WIPO . |

OTHER PUBLICATIONS

Graham et al., 1996, Soc. for Neuroscience 22:Abstr. 818.15.
Tsujii and DuBois, 1995, Cell 83:493–501.
Lundberg et al., 1997, Nature Med 3:30–31.
Crowe et al., 1997, Nature Med. 3:73–76.
Adams et al., 1996, J. Neurochem. 66:6–13.
Aisen et al., 1996, Dementia 7:201–206.
Anderson et al., 1996, The Journal of Neuroscience 16(5):17170–1719.
Chang et al., 1996, Neurobiology of Aging (17)5:801–808.
Li et al., 1996, Brain Research 738:196–204.
McGreer et al., 1996, Neurology 47:425–432.
Nakayama et al., 1996, Society for Neuroscience 22:1670.
Kaufman et al., 1996, Proc. Natl. Acad. U.S.A. 93:2317.
Pasinetti et al., 1996, Neurobiology of Aging 17(5):707–716.
Paul S. Aisen, 1995, Dementia 9(2):173–182.
Anderson et al., 1995, Journal of Neurochemistry 65(4):1487–1498.
Oda et al., 1995, Alzheimer's Research 1:29–34.
Aisen and Davis, 1994, Am J. Psychiatry 151(8):1105–1113.
Anderson et al., 1994, Experimental Neurology 125:286–295.
Loo et al., 1993, Proc. natl. Acad. Sci. USA 90:1–5.
Rogers et al., 1993, Neurology 43: 1609–1611.
Yamagata, 1993, Neuron 11:371–386.
Merck Index, p. 1125, No. 6640 Nimesulide.
IBC's Industry Symposium on COS–2 Inhibitors, Aug. 6–7, 1998, San Diego, CA, abstract by Dr. Pasinetti.
Mattson, 1998, Science & Medicine Mar./Apr.:16–25.
McGeer and McGeer, 1998, Neurol. Rev.1(Suppl.):8–11.
Needleman and Isakson, 1998, Science & Medicine Jan./Feb.:26–35.
Lukiw and Bazan, 1997, Soc. for Neurosci. Abstracts 23:2171.
Lukiw and Bazan, 1997, J. Neurosci. Res. 50:937–945.
Fagarasan and Aisen, 1996, Brain Res. 723:231–234.
Nakayama et al., 1996, Soc. for Neurosci. Abstracts 22:1670.
Rabasseda, 1996, Drugs of Today 32:365–384.
Tocco et al., 1996, Soc. for Neurosci. Abstracts 22:215.
Yang et al., 1996, J. Am. Soc. Nephrol. 7:1652. (Abstract only).
Nakayama et al., 1995, Soc. for Neurosci. Abstracts 21:1268.
Smale et al., 1995, Exp. Neurol. 133:225–230.
Zhu et al., 1995, Soc. for Neurosci. Abstracts 21:300.
Murphy et al., 1989, Neuron 2:1547–1558.

*Primary Examiner*—Theodore J. Criares
*Attorney, Agent, or Firm*—Richard S. Clark

[57] ABSTRACT

The present invention relates to the use of nimesulide and structurally related compounds in the prevention and/or treatment of neurodegenerative conditions. It is based, at least in part, on the discovery that nimesulide exhibits a neuroprotective effect against β-amyloid induced cell death. Without being bound to any particular theory, it appears that nimesulide inhibits a non-inflammatory mechanism of neurodegeneration.

9 Claims, 24 Drawing Sheets

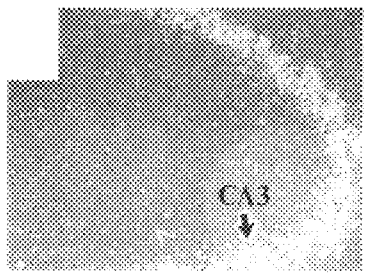 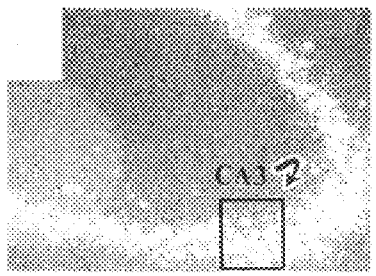 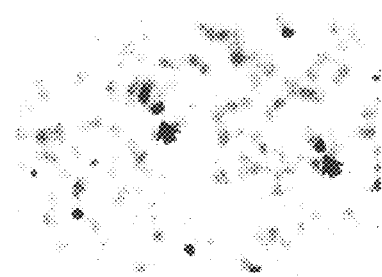
FIG.7A  FIG.7B  FIG.7C
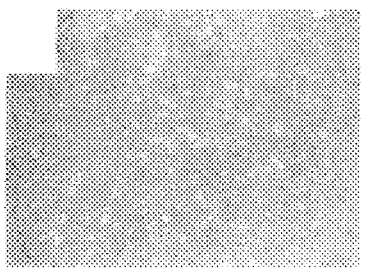 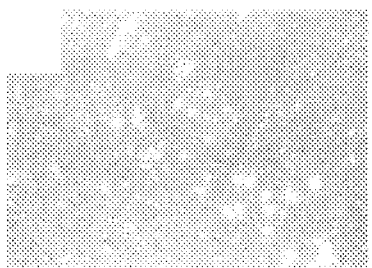 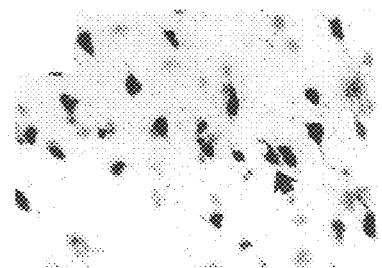
FIG.7D  FIG.7E  FIG.7F
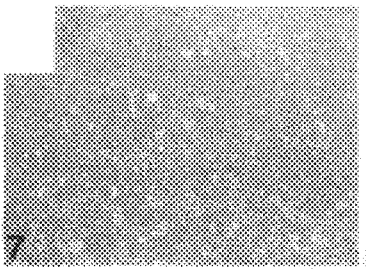 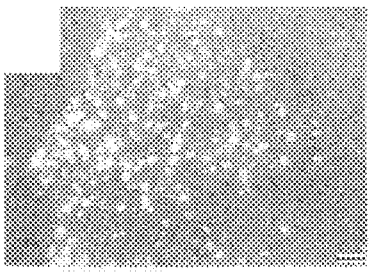 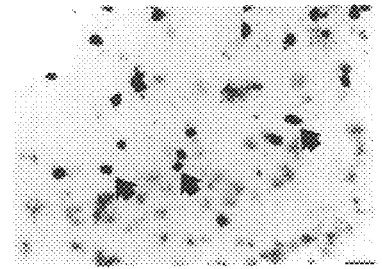
FIG.7G  FIG.7H  FIG.7I

TREATMENT OF NEURODEGENERATIVE CONDITIONS WITH NIMESULIDE This application claims benefit of provisional application Ser. No. 60/033,332, filed Nov. 21, 1996.

1. INTRODUCTION

The present invention relates to the use of nimesulide and structurally related compounds in the prevention and/or treatment of neurodegenerative conditions such as Alzheimer's Disease. It is based, at least in part, on the discovery that nimesulide, in effective concentrations, inhibits cell death.

2. BACKGROUND OF THE INVENTION
2.1. ALZHEIMER'S DISEASE

Sporadic Alzheimer's Disease is the major neurodegenerative disease associated with aging, the risk of developing the disease rising exponentially between the ages of 65 and 85, doubling every five years. Histologically, the hallmarks of Alzheimer's Disease are the deposition of amyloid in senile plaques and in the walls of cerebral blood vessels; the presence of neurofibrillary tangles, and neurodegeneration. The etiology of Alzheimer's Disease, however, is not well understood. Genetic factors have been proposed to play a role, including trisomy 21, mutations in the amyloid β-protein precursor ("APP") gene, the presenilin-1 (PS1) and presenilin-2 (PS2) genes, and the presence of the apolipoprotein E type 4 allele (Younkin, 1995, Ann. Neurol. 37:287–288; Lendon et al., 1997, JAM A 277:825). Several studies have indicated that β-amyloid induces apoptosis in cultured neurons (Loo et al., 1993, Proc. Natl. Acad. Sci. U.S.A. 90:7951–7955; Li et al., 1996, Brain Res. 738:196–204). Such induction may involve the immediate early gene proteins, c-jun and fos (Anderson et al., 1995, J. Neurochemistry 65:1487–1498; Anderson et al., 1994, Experimental Neurology 125:286–295; Anderson et al., 1996, J. Neurosci. 16:1710–1719).

It has been proposed that apoptosis may be involved in the pathogenesis of Alzheimer's disease Smale et al., 1995, Exp. Neurol. 133:225–230; Anderson et al., 1996, J. Neurosci. 16:1710–1719; Anderson et al., 1994, Exp. Neurol. 125:286–295. Inflammatory mechanisms have also been implicated; (Pasinetti, 1996, Neurobiol. Ageing 17:707–716) supportive of such a mechanism are the observations that acute phase proteins are elevated in the serum of Alzheimer's Disease patients, and are deposited in amyloid plaques; activated microglial cells tend to localize in the vicinity of senile plaques, and complement components have been localized around dystrophic neuntes and neurofibrillary tangles (Aisen and Davis, 1994, Am.J.Psychiatry 151:1105–1113). Antuinflammatory agents have been suggested as potential therapeutic agents (Aisen et al., 1996, Dementia 7:201–206; McGeer et al., 1996, Neurology 47: 425–432). Because they tend to have fewer adverse side effects, selective inhibitors of the enzyme cyclooxygenase-2 have been advanced as agents for treating such inflammation (International Publication No. WO 94/13635 by Merck Frosst Canada Inc.). Prior to the present invention, however, it had not been believed that such agents could be used to inhibit non-inflammatory aspects of neurodegeneration in the context of Alzheimer's Disease or otherwise.

2.2. CYCLOOXYGENASE-2

Cyclooxygenases ("COXs") are enzymes that catalyze the formation of prostaglandin ("PG")-$H_2$ from arachidonic acid (AA). PG-$H_2$ is further metabolized to physiologically active PGs (e.g., PG-$D_2$, PG-$E_2$ and PG-$F_{2\alpha}$), prostacyclin (PG-$I_2$) and thromboxanes. Specific PGs have diverse, often antagonistic effects on different tissues. For example, PG-$I_2$ and PG-$E_2$ are potent vasodilators that may contribute to the inflammatory response, whereas PG-$F_{2\alpha}$ is a vasoconstrictor.

There are two known COX isoforms, COX-1 and COX-2, which, though physiologically distinct, are similar in amino acid sequence and enzymatic functions. COX-1 is constitutively expressed at different levels in different cell types. COX-2, however, is not constitutively expressed, and is generally undetectable in normal peripheral tissues (Kujubu et al., 1991, J. Biol. Chem. 266:12866–12872; O'Banion et al. 1992, Proc. Natl. Acad. Sci. U.S.A. 89:4888–4892). Rather, COX-2 expression is inducible (for example, by mitogens) and COX-2 mRNA levels have been observed to rise rapidly in response to inflammatory stimuli such as interleukin-1β and lipopolysaccharide, and to decrease in response to glucocorticoids. When subjected to these same factors, COX-1 mRNA levels remain substantially unchanged, suggesting that COX-2 is the isoform which mediates inflammation (Cao et al., 1995, Brain Res. 697:187–196; O'Banion et al. 1992, Proc. Natl. Acad. Sci. U.S.A. 89:4888–4892).

Recent evidence suggests that COX-2 may play a role in mechanisms of cell survival and cell adhesion in peripheral cells (Lu et al., 1996, Proc. Natl Acad. Sci. U.S.A. 92:7961–7965; Tsujii et al., 1995, Cell 83:493–501). Tsuji et al. reports that epithelial cells engineered to express elevated levels of COX-2 were resistant to butyrate-induced apoptosis, exhibited elevated BCL2 protein expression, and reduced transforming growth factor β2 receptor levels (Tsuji et al., 1995, Cell 83:493–501). Lu et al. indicates that non-steroidal antiinflammatory drugs may induce an apoptotic mechanism involving the COX system.

The roles of COX-1, COX-2 and PG synthesis in normal brain, and in the context of Alzheimer's Disease, have not been fully characterized to date. The importance of PGs in brain physiology may be independent of inflammatory mechanisms. In the brain, PG receptors have been identified in the hypothalamus, thalamus, and limbic system (Watanabe et al., 1989, Brain Res. 478:143–148). PGs are involved in hypothalamic-pituitary hormone secretion (Kinoshita et al., 1982, Endocrinol. 110:2207–2209), regulation of temperature and the sleep-wake cycle (Hayaishi, 1988, J. Biol. Chem. 263:14593–14596). There is recent evidence that COX-2 mRNA is expressed and regulated in rat brain by synaptic activity and glucocorticoids (Adams et al., 1996, J. Neurochem. 66:6–13; Kaufmann et al., Proc. Natl. Acad. Sci. U.S.A. 93:2317–2321; Yamagata et al., 1993, Neuron 11:371–386). These studies indicate that COX-2 is regulated as an immediate early gene in the brain, and suggest that PGs may be important in trans-synaptic signalling and long-term potentiation. Chang et al. (1996, Neurobiol. of Aging 17:801–808) report that COX-2 mRNA expression is decreased in Alzheimer's disease.

3. SUMMARY OF THE INVENTION

The present invention relates to the use of nimesulide and structurally related compounds in the prevention and/or treatment of neurodegenerative conditions. It is based, at least in part, on the discoveries that (i) COX-2 expression in models of neurodegeneration is increased in neurons rather than glial cells (consistent with a non-inflammatory mechanism), and (ii) nimesulide exhibits a neuroprotective effect against β-amyloid induced neuronal cell death. This latter finding is particularly unexpected in view of the ability of COX-inhibitors to increase apoptosis of non-neuronal cells. Without being bound to any particular theory, it appears that nimesulide inhibits a non-inflammatory mechanism of neurodegeneration.

4. DESCRIPTION OF THE FIGURES

FIG. 1. Regional expression of COX-2 mRNA in control unlesioned male rat brain. COX-2 mRNA expression was assessed by in situ hybridization and visualized by X-ray autoradiography. Abbreviations: DG, dentate gyrus; CA1, CA2 and CA3 subregions of the neuronal pyramidal layer of the hippocampal formation; PAC, parietal cortex; PYC, pyrifoni cortex; AC, amygdaloid complex; THAL, ventroposterior thalamic nucleic. Adapted from plate 24 of Paxinos and Watson, 1986 (*The Rat Brain in Steriotaxic Coordinates*, Academic Press, NY).

Figure 2:
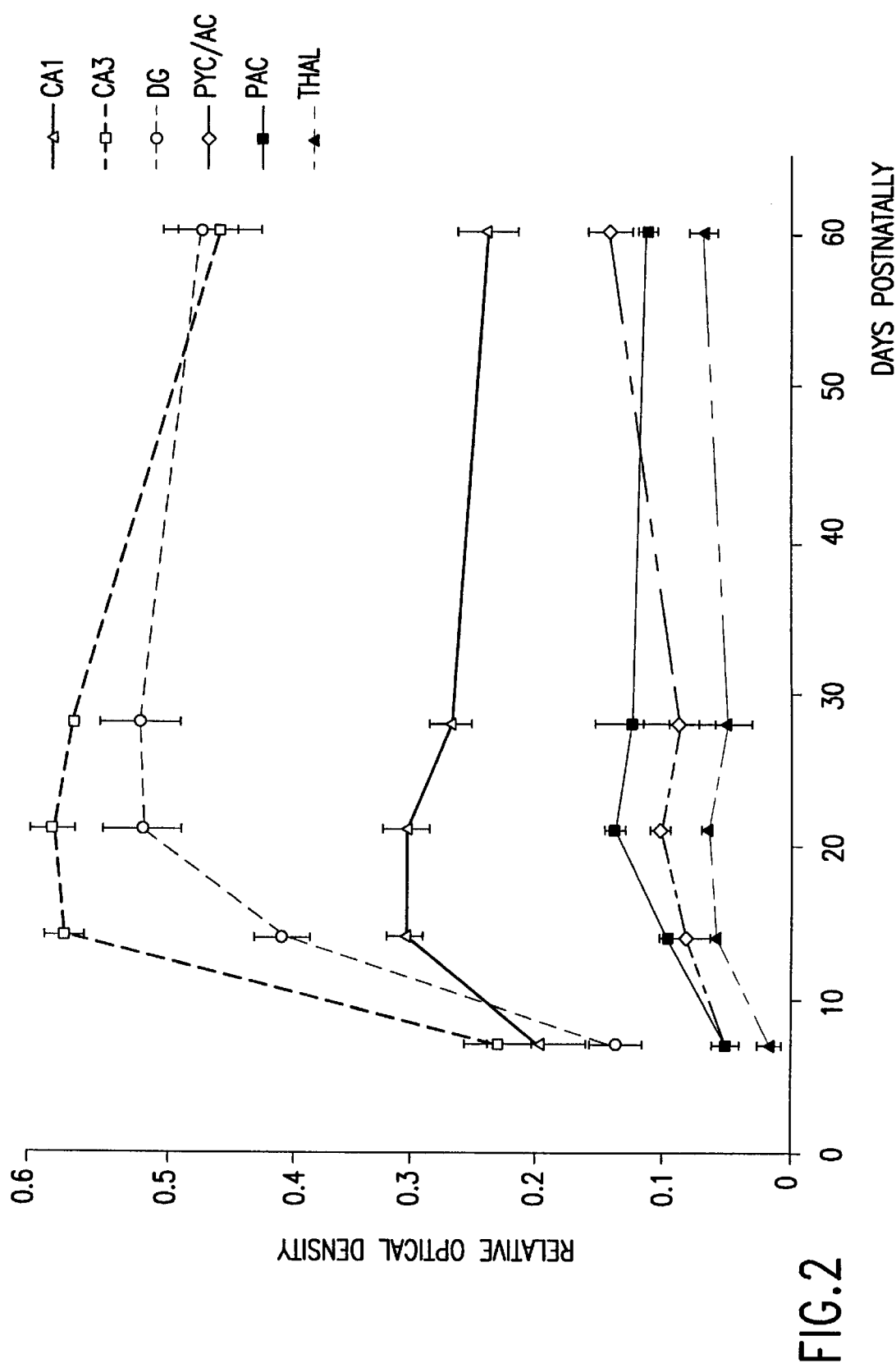

FIG. 2. Maturational regulation of COX-2 mRNA expression in rat brain. Optical densities were quantified from autoradiographic images. Abbreviations, as above and as follows: PYC/AC, pyriform and amygdaloid complex that were quantified for COX-2 mRNA expression as a single brain region. N=5–8 per time point.

Figure 3:
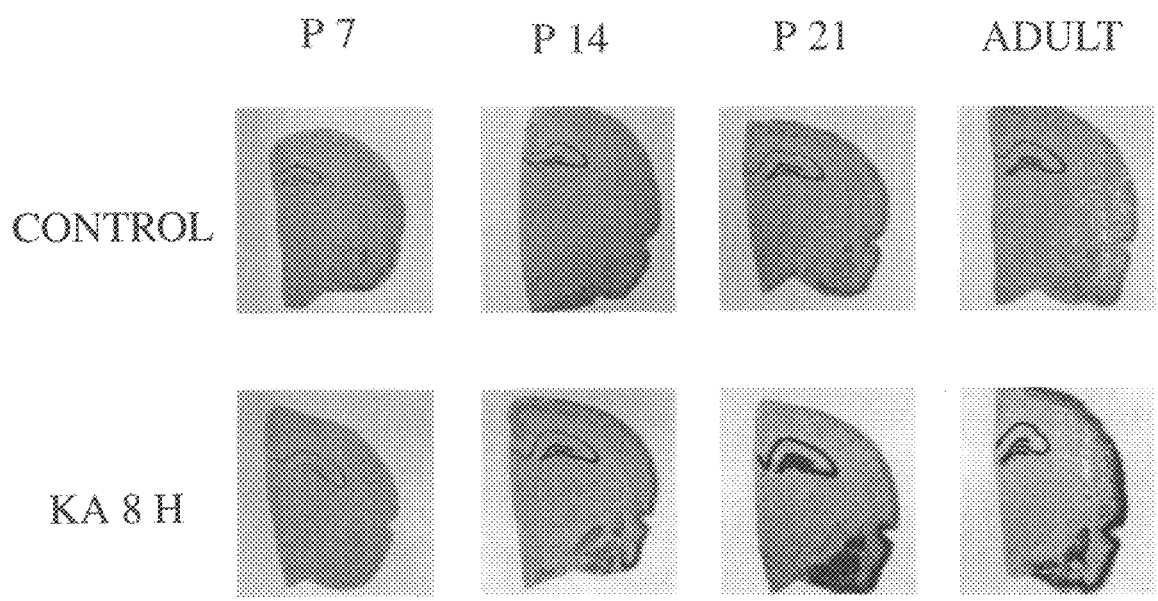

FIG. 3. Maturational influence on COX-2 mRNA expression during response to KA-induced seizures. Micrographs were generated from autoradiographic images. For anatomical distribution of changes, refer to FIG. 1. Control, unlesioned vehicle-injected rats; KA 8 H, KA-treated rats 8 hours prior to sacrifice; postnatal days P-7, P-14, and P-21.

FIG. 4 A–D. Time course of COX-2 mRNA changes in rat brain during responses to KA treatment: maturational influences and regional distribution of changes. Optical densities were quantified from autoradiographic images. Data are expressed as means±SEM, N=4=6 per group. *P<0.01 vs 0 H group (saline injected group); 4h, 8h, 16h, 30h, 120h, time in hours after onset of KA-induced seizures.

FIG. 5 A–D. Maturational influence on the distribution of COX-2 mRNA expression and induction in rat hippocampus. COX-2 mRNA in P21 (A,B) and adult (C,D) hippocampal formations as assessed by in situ hybridization assay and visualized by emulsion autoradiography using dark-field illumination. In A and C, COX-2 mRNA expression in control rats (vehicle injected); in B and D, COX-2 mRNA 8 hours after onset of KA-induced seizures. Arrows point toward the superficial layer of the DG (stratum granulosum). Scale bar=200 μm.

Figure 6:
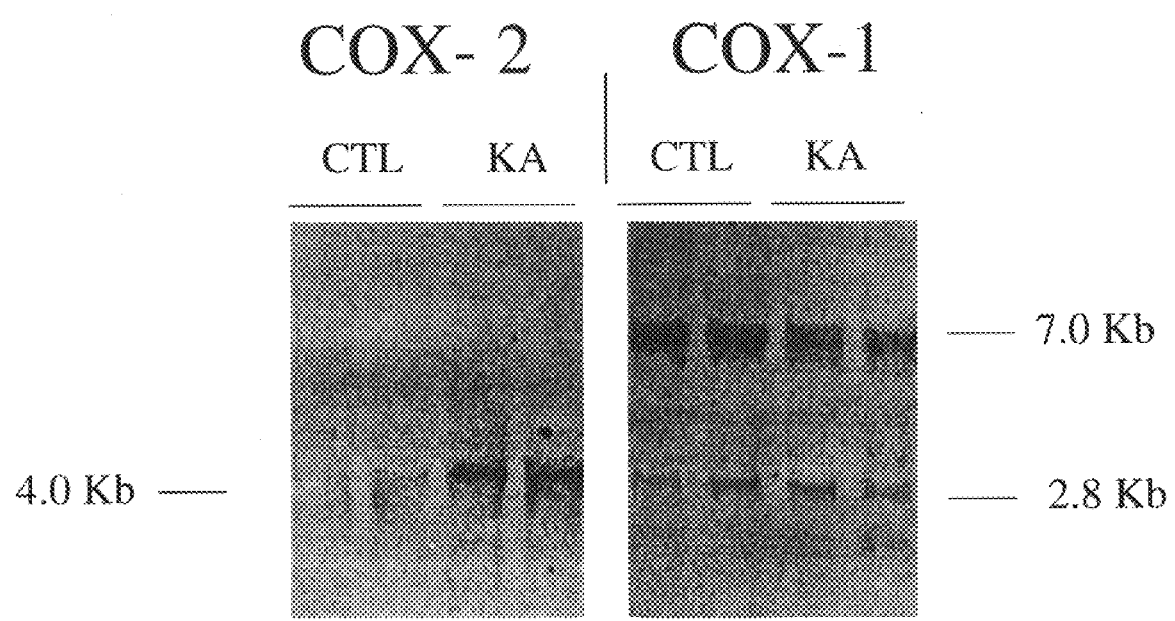

FIG. 6. Selective induction of hippocampal COX-2 but not COX-1 mRNAs during response to KA-induced seizures as assessed by gel blot hybridization assay. CTL, control saline-injected rats; KA, KA-treated rats 12 hours post lesioning.

FIG. 7 A–I. KA-induced COX-2 and apoptosis in adult rat brain. In (A,B), COX-2 mRNA expression in CA3 hippocampal pyramidal neurons of control and KA-treated rat, respectively; in (C), CA3 subregion of the hippocampal formation of KA-lesioned rats showing neurons with apoptotic features (arrows). In (D,E), COX-2 mRNA expression in pyriform cortex of control and KA-treated rat respectively. In (F), arrows point toward apoptotic cells of pyriform cortex of KA-lesioned rats. In (G,H), COX-2 mRNA expression in cells of the amygdaloid complex of control and KA-treated rats, respectively. In (I), arrows point toward apoptotic cells of the amygdaloid complex of KA-lesioned rats. COX-2 mRNA was assayed by in situ hybridization and visualized by emulsion autoradiography under dark field illumination. In situ 3' end-labeling was used to assess apoptotic features following KA treatment. Scale bar: in A,B,D,E,G,and H=200 μm; in C,F and I=40 μm.

FIG. 8 A–D. Immunocytochemical evidence of neuronal COX-2 expression/regulation in response to glutamate in vitro. COX-2-like immunoreactivity in monotypic cultures of rat primary hippocampal neurons in (A) control and (B) after glutamate exposure (12 hours). In (C,D) control and glutamate treated cultures immunoreacted with immunoadsorbed COX-2 antibody, respectively. Scale bar=50μm.

FIG. 9 A–C. Effect of nimesulide on endotoxin-mediated synthesis/secretion of cytokines and nitrites in glia. The effect of $10^{-9}$ M nimesulide on the synthesis/secretion of (A) TNF, (B) NO intermediates (Griess reaction) and (C) $PGE_2$, as assessed in BV2 mouse immortalized microglial cells. Mean±SEM, n=8–10 per group. Lipopolysaccharide ("LPS")=5 μg/ml. LPS and nimesulide were added in combination to cultures; incubation time was 24 hours. Statistics used ANOVA, p<0.05.

FIG. 10 A–E. Time course of changes of COX-2 protein in P19 cells during response to conditions leading to apoptotic death. In (A), quantitative analysis of COX-2 induction in P19 cells, n=4–6 per group, p<0.05 vs. t=0. In (B), changes were assessed by western analysis, using chemiluminescent detection. In (C,D) the morphological appearance of apoptotic nuclei in P19 cells was assessed by Hoechst H33258 24 hours after serum removal (and replacement with N2 medium). In (E), the electrophoretic profile of DNA showing DNA laddering degradation was assessed 14 hours after serum removal (lane 1, control cells at t=0; lane 2, DNA laddering 14 hours after serum removal; lane 3, DNA markers). The COX-2 polyclonal antibody used in these studies was as described in Section 6. The COX-2 specific antibody recognizes two major bands having estimated molecular weights of about 70 and 65 kDa in total homogenates of mouse, rat and human brains.

FIG. 11A–D. Regulation of COX-2 during response to Aβ1-40 mediated oxidative stress in SH-SY5Y neuronal cells. (A) Dose-dependent Aβ1-40 mediated neurotoxicity, as assessed by MTT assay. Aβ1-40 was aggregated for 24 hours at 37° C., incubation of SH-SY5Y cells was for 48 hours. (B) SH-SY5Y cells were incubated with 10 or 20 μm Aβ1-40 (lanes 2 and 3, respectively), revealing a sharp induction of COX-2 expression by 48 hours after treatment, compared to untreated controls (lane 1), as assessed by western blot analysis. (C) the same blot used in (B) was immunoreacted with β-actin antiserum. (D) The same SH-SY5Y cultures used for western analysis were examined for apoptotic mechanisms. DNA degradation coincided with induction of COX-2 expression (lane 1, control, lanes 2, 3 SH-SY5Y cells treated with Aβ1-40).

Figure 12:
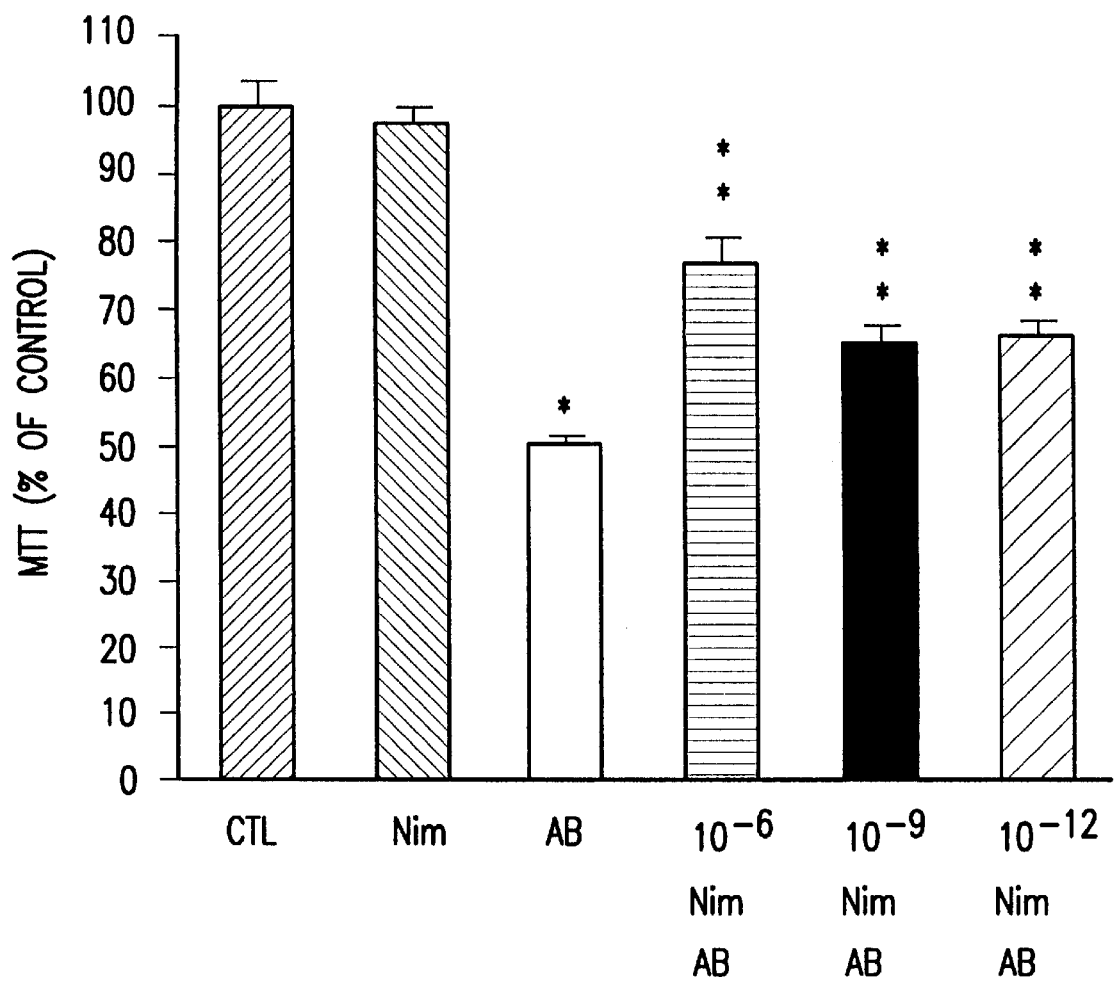

FIG. 12. Protective effect of nimesulide on Aβ1-40 mediated neurotoxicity as assessed by MTT assay using SH-SY5Y neuronal cells. Abbreviations: CTL control; NIM nimesulide; A B-β-amyloid (1-40). *P<0.01 vs CTL, **P<0.05 vs. CTL.

Figure 13:
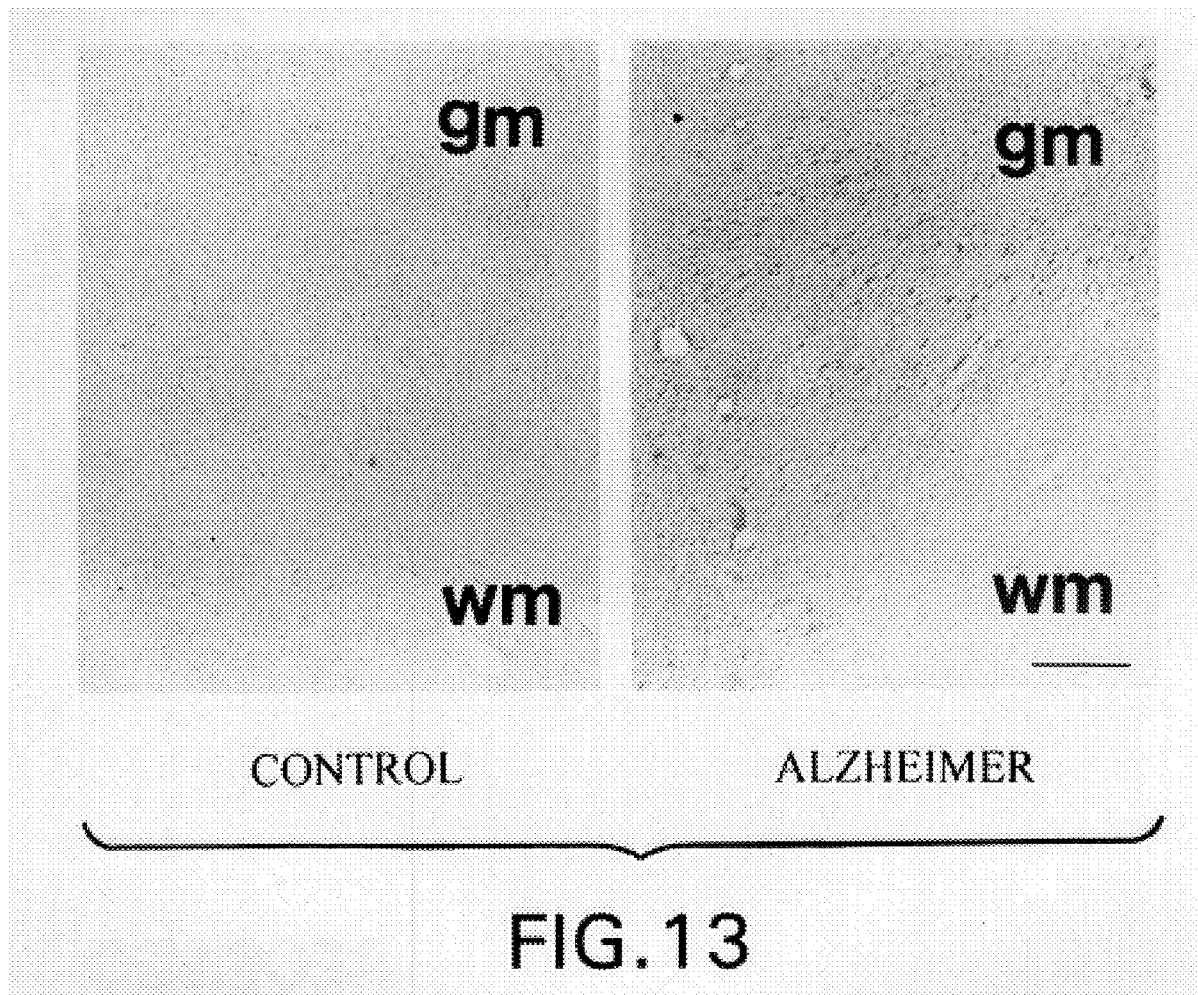

FIG. 13. Micrographs showing induction of COX-2 immunoreactivity in temporal cortex of AD and age-matched neurological controls. The micrographs show a selective induction of COX-2 immunostaining in neuron-rich grey matter ("gm") but not glia-rich white matter ("wm") regions.

FIG. 14 A–D. COX-2 immunostaining of neurons in temporal cortex of AD brain and co-localization of COX-2 immunostaining with vessels and AD plaques in hippocampal formation in AD brains. In (A,B), immunostaining of COX-2 neurons of AD are shown (A, low power; B, high power magnification). In (C), immunostaining of vessels. In (D), COX-2 in AD plaques as assessed by Aβ immunostaining on adjacent tissue sections.

Figure 15A:
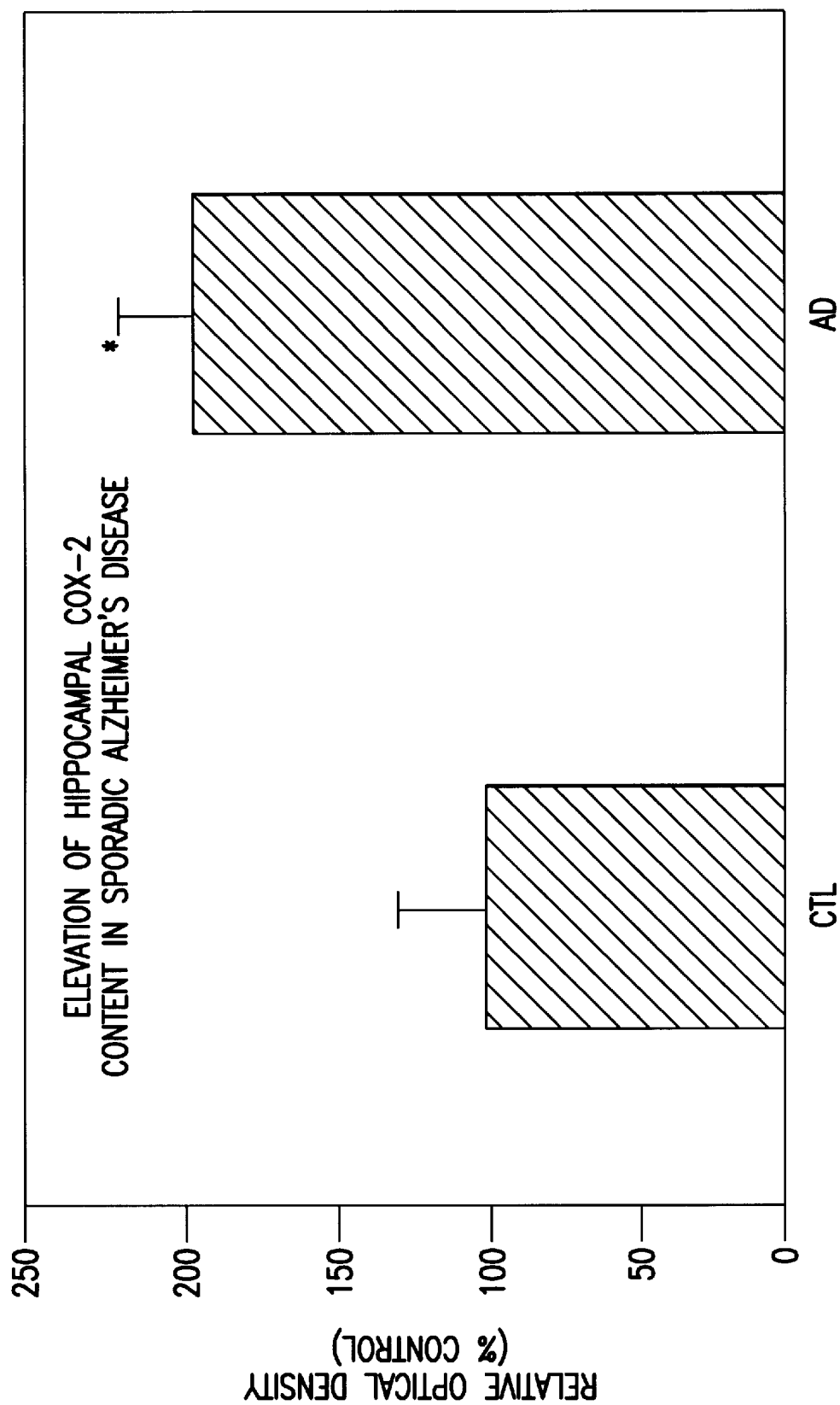
Figure 15B:
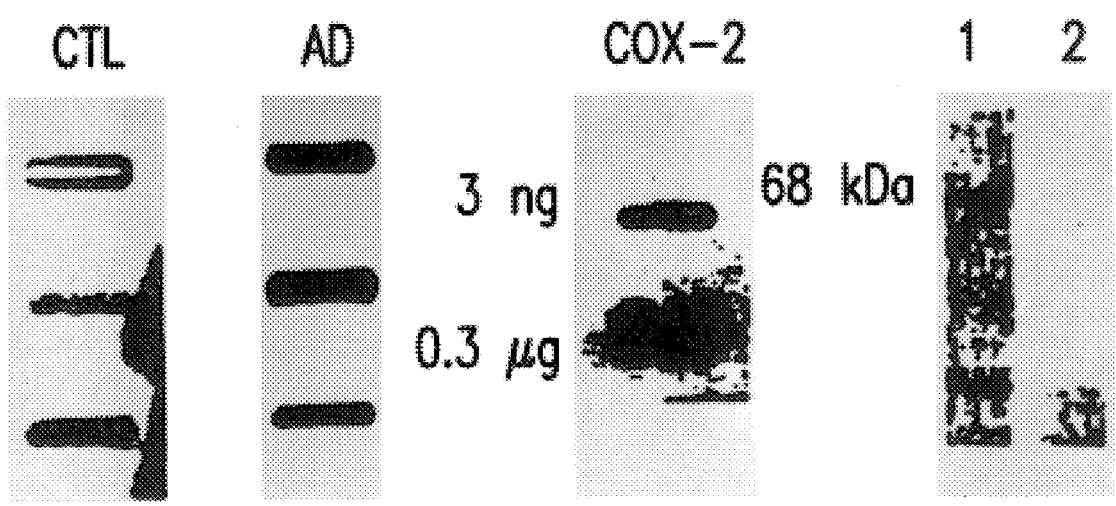

FIG. 15 A–B. Elevation of hippocampal COX-2 content in AD as assessed by dot-blot analysis with chemiluminescence detection. In (A), a histogram is shown which demonstrates 2-fold elevation of COX-2 content in AD relative to control cases ("CTL"). Frozen tissues were from autopsy-confirmed caucasian cases of sporadic AD and CTL. AD: age range 69–93 years. Post-mortem delay in AD cases: 5.2±1 hours. CTL: age range 53–82 years. Post mortem delay in CTL cases: 8.5±1 hours. p<0.05 vs. control. In (B), representative signals from AD and CTL samples (50 μg total protein loaded) and purified COX-2 peptide (3 ng and 3000 ng). COX-2 antibody recognized two major bands of about 65 and 70 kDa (B, lane 1); the COX-2 signal was abolished by immunoadsorption of COX-2 antibody with purified COX-2 peptide (B, lane 2).

Figure 16:
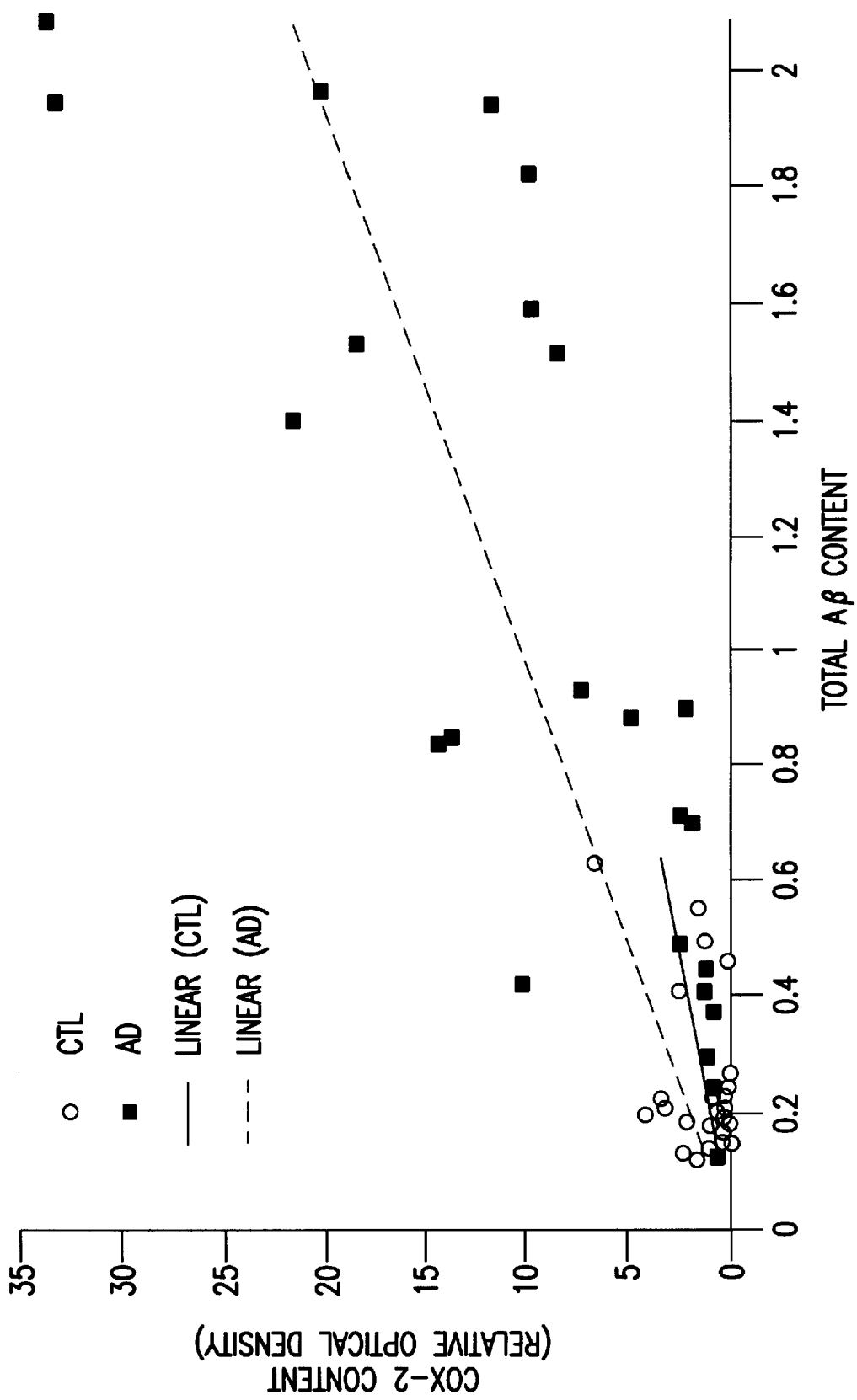

FIG. 16. Correlation of hippocampal COX-2 and total Aβ content in AD brain. The same brain homogenates as used in FIG. 13 were used to compare levels of COX-2 and total amyloid β content.

Figure 17A:
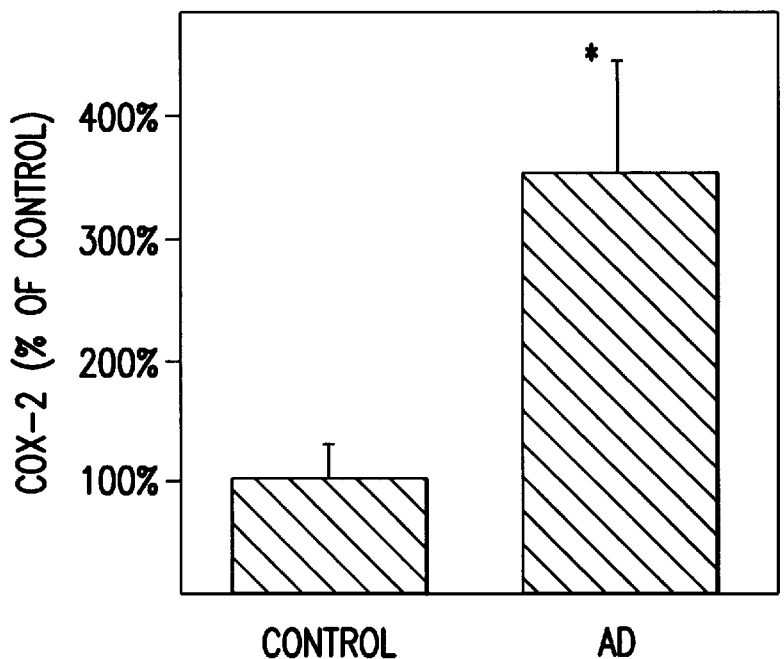

FIG. 17A and B. Cortical regulation of COX-2 in Alzheimer's Disease. (A) The regulation of COX-2 was assessed in frontal cortex of Alzheimer's Disease patients (N=14) compared to elderly neurological controls (n=13). Autopsy confirmed Alzheimer's Disease and age-matched control brains were obtained from the Alzheimer's Disease Brain Bank of the Department of Psychiatry, Mount Sinai School of Medicine. (B) Expression of action was used as a control *<P0.02 (t-test).

Figure 18:
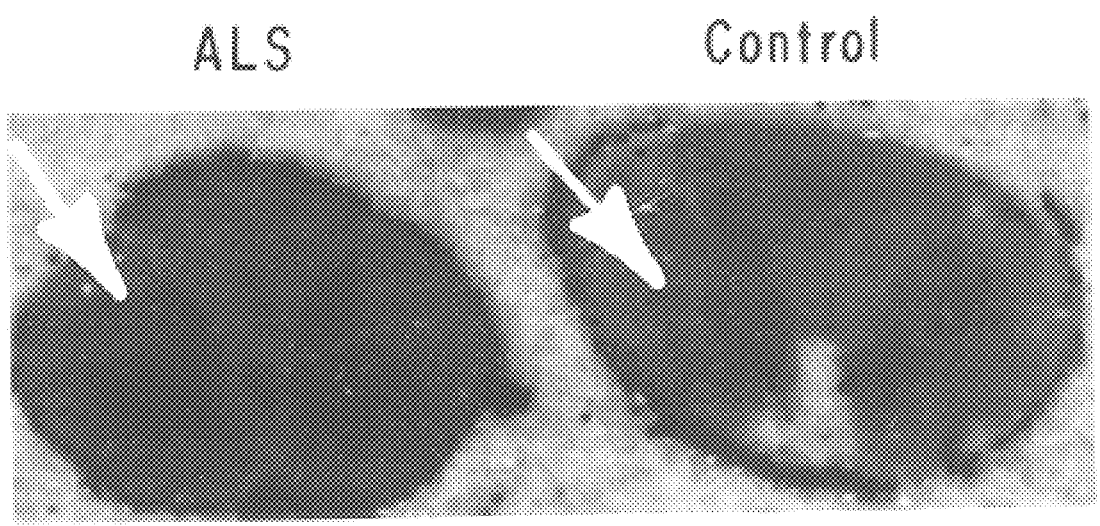

FIG. 18. COX-2 mRNA regulation in neurons of the anterior and posterior horn of the spinal cord of ALS and neurological controls. Autoradiographic images were visualized by X-ray film. The arrow pointed toward the ventral horn shows intense induction of COX-2 mRNA signal in the ALS case.

Figure 19A:
Figure 19B:
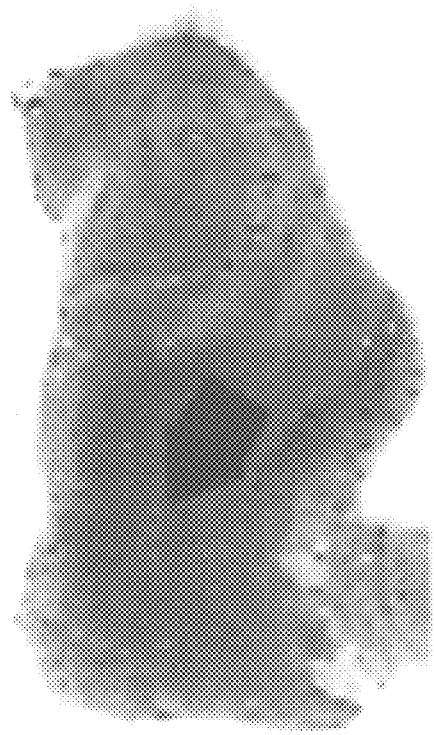

FIG. 19A and B. COX-2 mRNA elevation in a biopsy of human cortical epileptic foci as assessed by in situ hybridization assay. Autoradiographic images were visualized by X-ray film. Arrow pointed toward the cortical layers showing intense COX-2 mRNA signal in epileptic brain (A) versus control (B).

5. DETAILED DESCRIPTION OF THE INVENTION

The present invention relates to the use of the cyclooxygenase-2 ("COX-2") selective inhibitor, nimesulide, and structurally related compounds in the prevention and/or treatment of neurodegenerative conditions. It is based, at least in part, on the discoveries that COX-2 expression increased in parallel with neuronal lesions produced by kainic acid and with induction of neuronal apoptosis in an established in vitro system (see Sections 6 and 8, below). Contrary to reports in the prior art that COX-2 plays a primary role in inflammation and may be involved in an inflammatory component of neurodegeneration (for example, in the context of Alzheimer's Disease), it has further been discovered that in the human brain, COX-2 expression appears to be restricted to neurons rather than to glial cells (whereas expression in glial cells would be expected if an inflammatory mechanism were operative: see Section 9, below). A correlation between COX-2 expression and the characteristic protein associated with Alzheimer's Disease, Aβ protein, has been observed (see Section 9). Further, it has been demonstrated that nimesulide exerts a neuroprotective effect against β-amyloid induced cell death in neuronal cultures. In view of these findings, according to the invention, nimesulide and related compounds may be used to intervene in the process of apoptotic neuronal cell death associated with Alzheimer's Disease and other neurodegenerative conditions.

The term "nimesulide", as used herein, refers to a compound, 4-nitro-2-phenoxymethanesulfonanilide, having a structure as set forth for Formula I below.

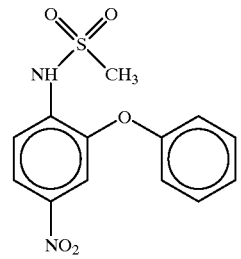

Compounds which are considered structurally related are compounds which have a similar bicyclic structure and which selectively inhibit COX-2. For example, substituents, analogs, and enantiomers of nimesulide are considered to be structurally related compounds. As a further example, a structurally related compound may compete with nimesulide for binding to COX-2, or may bind to substantially the same location of COX-2, as determined crystallographically. Moreover, nimesulide, conjugated to another compound, is also considered to be a structurally related compound as defined herein.

Nimesulide, or a structurally related compound, may be administered so as to provide an effective concentration in the nervous system of the subject being treated. An effective concentration is defined herein as that concentration which inhibits neuronal cell death by at least 20 percent. In specific, nonlimiting embodiments of the invention, the concentration of nimesulide is at least 1 nanomolar, and preferably at least 1 micromolar in the location of neuronal cells which are desired to be treated. Desirably, the concentration of nimesulide is less than $10^{-3}$ molar to avoid toxicity. In one such specific embodiment, where the neurodegenerative condition to be treated is Alzheimer's Disease, the concentration of nimesulide in the hippocampal formation of the subject is at least 1 nanomolar, and preferably at least 1 micromolar. Equivalent amounts of structurally related compounds (adjusted to compensate for differences in potency) may also be used.

Nimesulide or a structurally related compound may be administered in any manner which achieves the desired effective concentration. For example, suitable routes of administration include oral, intravenous, subcutaneous, intramuscular, transdermal and intrathecal routes.

Nimesulide or a structurally related compound may be comprised in a suitable pharmaceutic carrier. Formulations may provide for sustained release.

For example, but not by way of limitation, nimesulide may be administered orally at doses of 2–800 mg/day, preferably 50–400 mg/day, and most preferably 200 mg/day.

Neurodegenerative conditions which may be treated according to the invention include, but are not limited to, Alzheimer's Disease, Parkinson's Disease, seizure-associated neurodegeneration, amyotrophic lateral sclerosis, spinal cord injury and other diseases wherein the condition is not conventionally regarded as an inflammation-mediated or autoimmune disorder.

6. EXAMPLE: MATURATIONAL REGULATION AND REGIONAL INDUCTION OF CYCLOOXYGENASE-2 IN RAT BRAIN

6.1. MATERIALS AND METHODS

Animals and excitotoxic lesions. Male adult Sprague/Dawley rats of different ages were maintained in a controlled light and temperature environment, with food and water ad libidum. In adult rats (250–300 g), hippocampal excitotoxic lesions were induced by subcutaneous injection of kainic acid ("KA"; 10 mg/kg, Sigma). Because KA uptake is higher in young rats relative to adults (Berger et al., 1986, in Schwartz and Ben-Ari, *Advances in Experimental Medicine and Biology*, Plenum, N.Y., pp. 199–209), KA doses were adjusted to produce maximal excitotoxicity without reaching lethal doses (from 2 mg/kg at postnatal day P-7 to 6 mg/kg at postnatal day P25). Saline injected rats were used as controls (0 hour time point).

COX-1 and COX-2 cDNA probes. Bluescript plasmid (Stratagene) containing the full length rat COX-1 cDNA (2.7 kb) was linearized by digestion with ClaI; PCRII plasmid (Invitrogen) containing the coding sequence for rat COX-2 (1.8 kb) was linearized by digestion with PflMI (Feng et al., 1 993, Arch. Biochem. Biophys. 307:361–368). Linearized plasmids were purified using Elu-Quick (Schleicher & Schuell) after agarose gel electrophoresis.

In situ hybridization. At various intervals after the onset of KA-induced seizures, the rats were sacrificed, and the brains quickly removed, rinsed in cold phosphate buffer (PBS, 10 mM, pH 7.4) and immersed in methylbutane at $-25°$ C. for three minutes. The brains were sliced into 10 micrometer sections, frozen, and the resulting frozen sections were mounted on polylysine-coated slides and stored at $-70°$ C. For immunocytochemistry ("ICC") or in situ hybridization ("ISH"), frozen sections were post-fixed in PBS containing 4 percent paraformaldehyde (30 minutes at room temperature) and then rinsed in PBS. For ISH, tissue sections were rinsed in 0.1IM triethanolamine ("TEA"), pH 8.0, incubated in acetic anhydride ("AAH"; 0.25% v/v in TEA, 10 minutes) and rinsed in TEA and PBS. Following AAH treatment, tissue sections were hybridized with [$^{35}$S]-cRNA probes (0.3 $\mu$g/ml, $2\times10^9$ dpm $\mu$g$^{-1}$) made from COX-2 linearized CDNA transcription vectors (Feng et al.,1993, Arch. Biochem. Biophys. 307:361–368). Sense strand hybridization was used as a control and gave negative results. Following hybridization for 3 hours at $50°$ C., stringent washes (0.1×SSC at $60°$ C.) and dehydration, slides were exposed to X-ray film for seven days for quantification. Slides were then exposed to NTB-2 emulsion (Kodak, Rochester, N.Y.) for microscopic analysis of COX-2 mRNA distribution. Following development, tissue sections were counterstained with cresyl violet. Film autoradiograms were analyzed quantitatively using an image analysis system with software from Drexel University (Tocco et al., 1992, Eur. J. Neurosci. 4:1093–1103). Statistics were calculated by ANOVA followed by additional posthoc analysis.

In situ end labeling. In parallel studies, paraformaldehyde-fixed brain tissue sections were dehydrated, air dried and incubated with dATP, dCTP, dGTP (0.2 mM), dTTP (13 $\mu$M), digoxigenin-11-dUTP and DNA polymerase I (Boehringer Mannheim) at 10 units/100 $\mu$l at $37°$ C. for 2 hours. The reaction was stopped by addition of 20 mM EDTA, pH 8.0. Sections were incubated at room temperature overnight with an alkaline-phosphatase-conjugated digoxigenin antibody (Genius System, Boehringer Mannheim) diluted 1:200 in 5 percent sheep serum diluted in 150 mM NaCl, 100 mM TRIS-HCl, pH 7.5. Colorimetric detection with nitro blue tetrazolium and 5-bromo-4-chloro-3-indolyl-phosphate was performed with the Genius System by the manufacturer's protocol (Sakhi et al.,Proc. Natl. Acad. Sci. U.S.A. 91:7525–7529).

Northern blot hybridization assay. RNA extraction was performed as follows. After sacrifice, rat brains were dissected and stored at $-75°$ C. prior to processing. Total RNA was extracted from pools of hippocampal tissue (Pasinetti et al., 1994, J. Comp. Neurol. 339:387–400). Briefly, tissues were homogenized for 1 minute in 4 M guanidinium thiocyanate, 25 mM sodium citrate (pH 7.5), 0.5% sarcosyl and 0.1 M $\beta$-mercaptoethanol, in a final volume of 0.5 ml. After acidified phenol/chloroform extraction and ethanol precipitation, the RNA pellet was rinsed consecutively with 70% and 100% ethanol. The purified RNA was then dissolved in 0.5% sodium dodecyl sulfate ("SDS") and stored at $-75°$ C. Total RNA was quantified in a UV spectrophotometer. Total RNA (5 $\mu$g) from tissue was electrophoresed on denaturing (0.2M formaldehyde) agarose gels and transferred to a nylon membrane (Nylon 66 plus; Hoeffer, San Francisco Calif.) in 2×SSC. Blot hybridization was carried out with $10^6$ cpm/ml of antisense COX-1 or COX-2 [$^{32}$P]-cRNA probes in 50% formamide, 1.5×SSPE, 1% SDS, 0.5% dry milk, 100 $\mu$g/ml yeast total RNA and 500 mg/ml salmon sperm DNA at $53°$ C. for about 15 hours. Blots were washed to a final stringency of 0.2×SSC, 0.2% SDS at $72°$ C. Blots were exposed to Kodak X-ray film (XAR-5) with intensifying screens at $-70°$ C.

Cell cultures. Hippocampal neuron cultures were derived from embryonic rat brain. E16–E18 embryos were dissected in Hank's balanced salt solution and cultured (Pasinetti et al.,1994, J. Comp. Neurol. 339:387–400; Peterson et al., 1989, Dev. Brain Rcs. 48:187–195). Culture media were changed every 3 days. For glutamate neurotoxicity studies, eight day old cultures were treated with glutamate (250 $\mu$M, Sigma) in the presence of 2.4 mM calcium ion and 0.8 mM magnesium ion. After 6 hours of glutamate exposure, culture medium was replaced with fresh medium; COX-2-like immunoreactivity was assessed in neurons 12 hours later.

Immunocytochemical detection of COX-2 in monotypic cultures of primary rat neurons. Control and glutamate treated cultures were post-fixed in PBS containing 4% paraformaldehyde (30 minutes, room temperature), rinsed in PBS, pre-treated with normal serum and incubated overnight at $4°$ C. with primary antibodies. COX-2 antisera (rabbit IgG) was raised against a synthetic peptide (CNASASHSRLDDINPT; SEQ ID NO:1) encompassing the C-terminal region of the murine COX-2. The antisera reacts with human and rat COX-2 but not with COX-1, as assessed by Western blot analysis. Vectastain ABC kit (Vector, Burlingame, Calif.) was used in subsequent steps to complete the diaminobenzene staining (Pasinetti et al.,1994, J. Comp. Neurol. 339:387–400). Immunoadsorption of COX-2 antisera with synthetic COX-2 peptides controlled for specificity; adsorption was carried out overnight at $4°$ C. with synthetic COX-2 peptides at 30 $\mu$g/ml.

6.2. RESULTS

COX-2 expression in adult rat brain. FIG. 1 shows by ISH that the regional distribution of COX-2 mRNA was most notable in limbic structures, but was also present in neocortex (consistent with the reports of Kaufmann et al., Proc. Natl. Acad. Sci. U.S.A. 93:2317–2321 and Yamagata et al., 1993, Neuron 11:371–386). In the hippocampal formation, COX-2 mRNA was selectively expressed in cells of the granule and pyramidal neuron layers. COX-2 mRNA expression was also found in the outer layer of the parietal cortex, the pyriform cortex and cells of the amygdaloid complex.

Maturational regulation of hippocampal COX-2 mRNA expression. ISH results indicated that during maturation, COX-2 mRNA expression is differentially regulated in subsets of cells of neuronal layers of the hippocampal formation (FIG. 2, FIG. 3 top). From postnatal days P7-P14, COX-2 mRNA showed greater than two-fold increase in the granule cell layer of the dentate gyrus and in the CA3 subdivision of the pyramidal cell layer (p<0.001, FIG. 2). Though the expression of COX-2 mRNA was lower in the other brain regions examined, the pattern of maturational expression was similar (FIG. 2). By postnatal day P21, COX-2 mRNA expression approximated adult levels in all subregions examined (FIG. 2, FIG. 3 top).

Figure 4A:
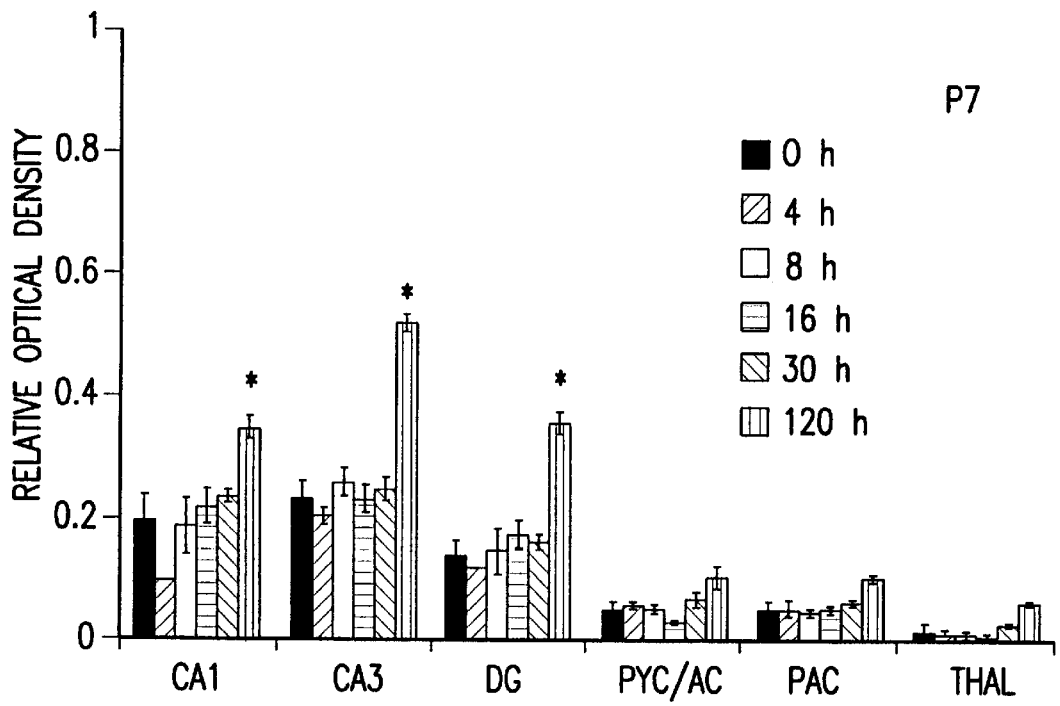
Figure 4B:
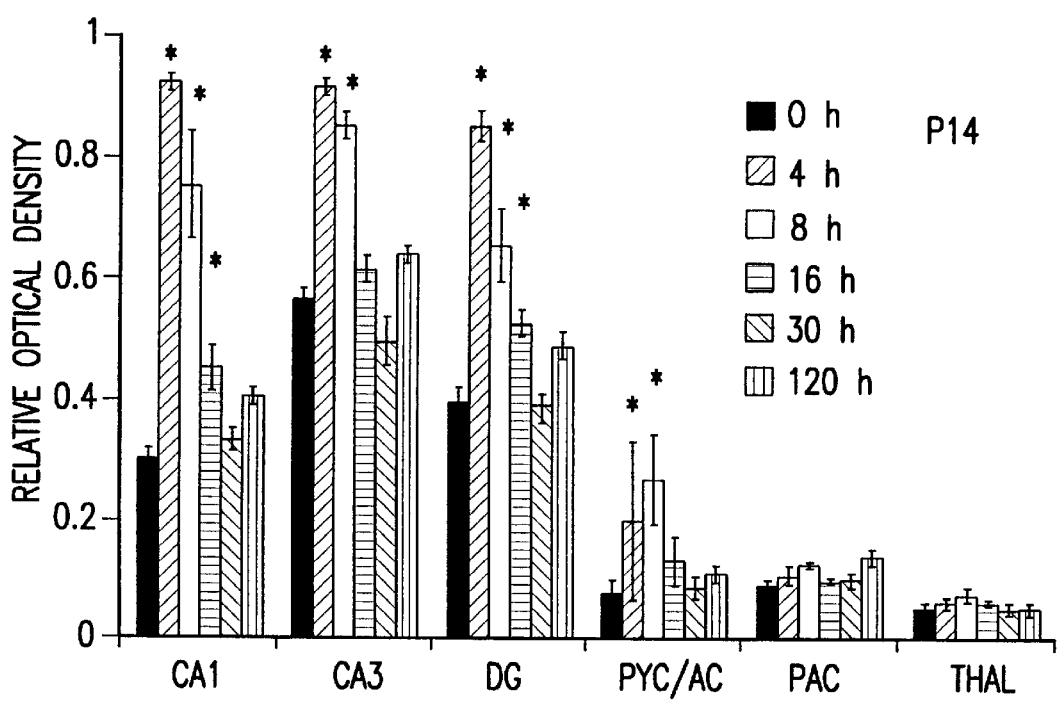
Figure 4C:
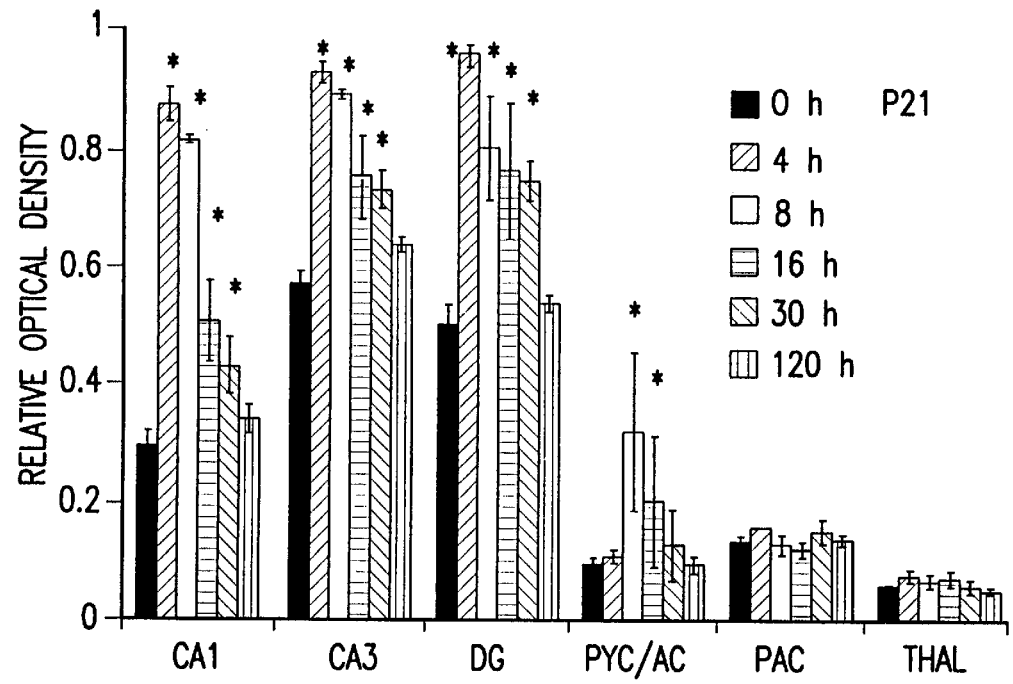
Figure 4D:
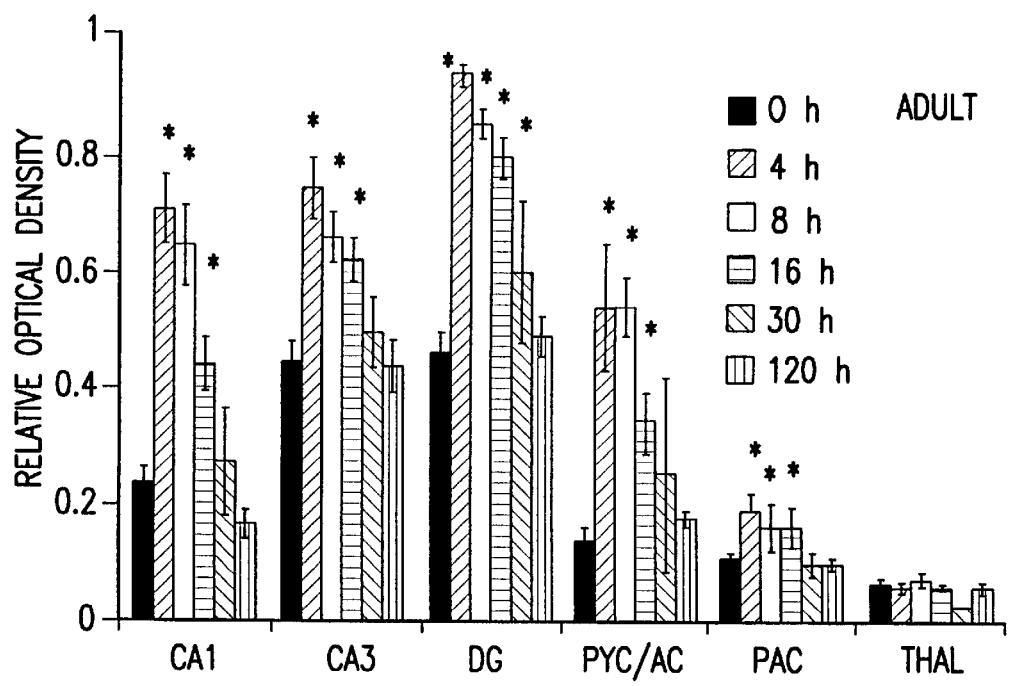

Response to KA-induced seizures. To further explore maturational regulation of COX-2 in brain, COX-2 mRNA expression during responses to KA-induced seizures was examined postnatally. Despite intense seizure activity after KA treatment, no detectable change of COX-2 mRNA expression was found in any brain region examined at P7 (FIG. 3, FIG. 4A). Changes in COX-2 mRNA expression at 120 hours post-KA treatment in the P7 group indicate developmental maturation rather than response to KA toxicity (FIG. 4A). In contrast to the P7 group, at P14 and P21 COX-2 mRNA increased within 4–8 hours after onset of KA-induced seizures in all the hippocampal subregions examined (FIGS. 4B and 4C). The level of COX-2 mRNA expression returned toward control levels within 120 hours after treatment in P14, P21 and adult rat brain.

Figure 5A:
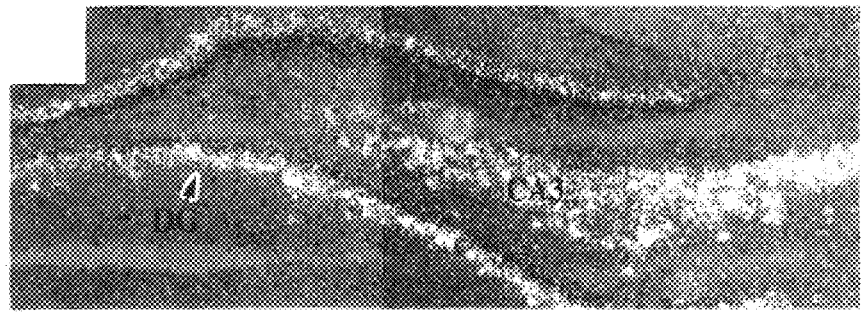
Figure 5B:
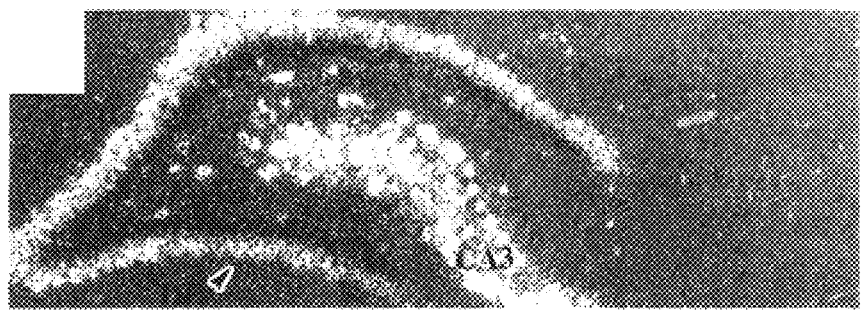
Figure 5C:
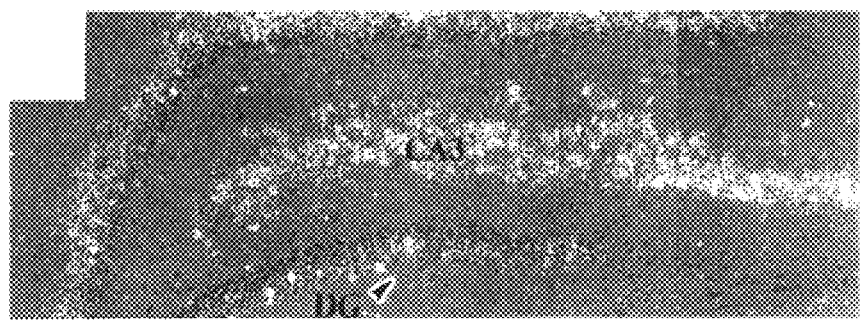
Figure 5D:
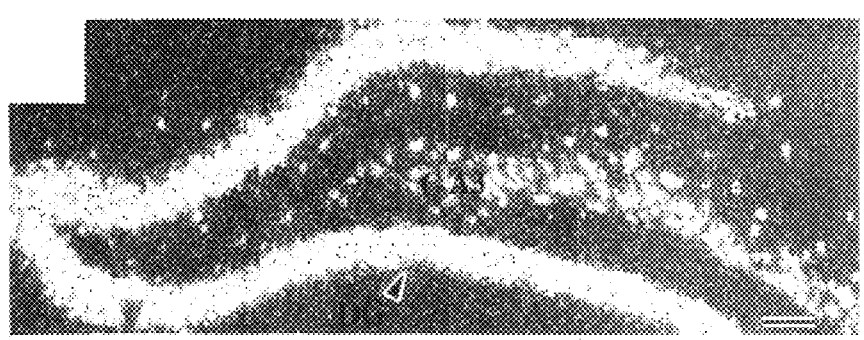

Within the dentate gyrus, control COX-2 expression in P14 and P21 rats was asymmetric, selectively localized to the more superficial neurons of the stratum granulosum rather than the deeper granule cells of the dentate gyrus blade (FIG. 5A). In response to KA treatment, COX-2 mRNA induction showed similar asymmetry of expression (FIG. 5B). In contrast, the asymmetry within the dentate gyrus was less notable in control animals and after KA-induction of the adult group (FIGS. 5C and 5D).

In parallel studies, northern blot hybridization of total RNA from hippocampus of adult rats 12 hours after KA-induced seizures confirmed COX-2 mRNA induction (FIG. 6). No detectable induction of COX-1 mRNA was found in the same rat brain (FIG. 6).

KA-induced COX-2 and apoptosis in adult rat. By 8 hours after onset of KA-induced seizures, COX-2 mRNA induction in cells of the CA3 region of the hippocampal formation (FIG. 7B), pyriform cortex (FIG. 7E) and amygdaloid complex (FIG. 7H) of the adult brain paralleled temporally and overlapped anatomically the onset of apoptosis as assessed by in situ end-labeling in the same brain regions (FIG. 7C, CA3 regions of the hippocampus; FIG. 7F, pyriform cortex; FIG. 7I, amygdaloid complex). Cellular COX-2 mRNA expression in adult, control (FIGS. 7A, 7D and 7G) and KA-treated (FIGS. 7B, 7E and 7H) rats was identified by emulsion autoradiography using ISH assays.

Figure 8A:
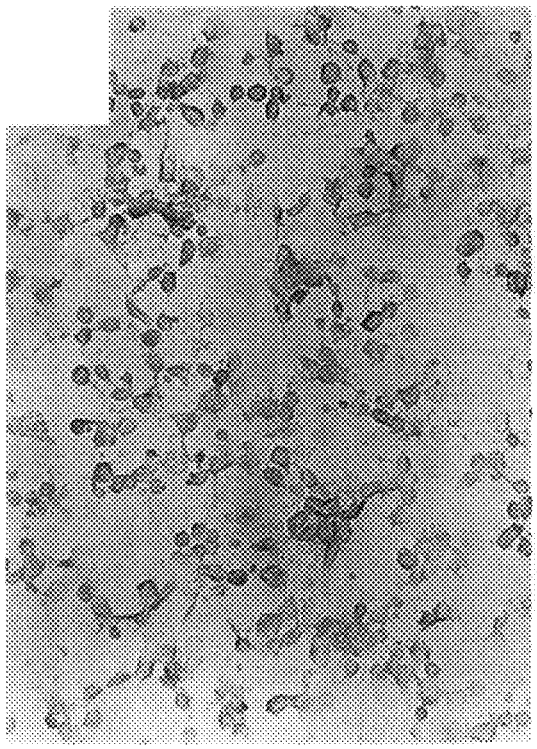
Figure 8B:
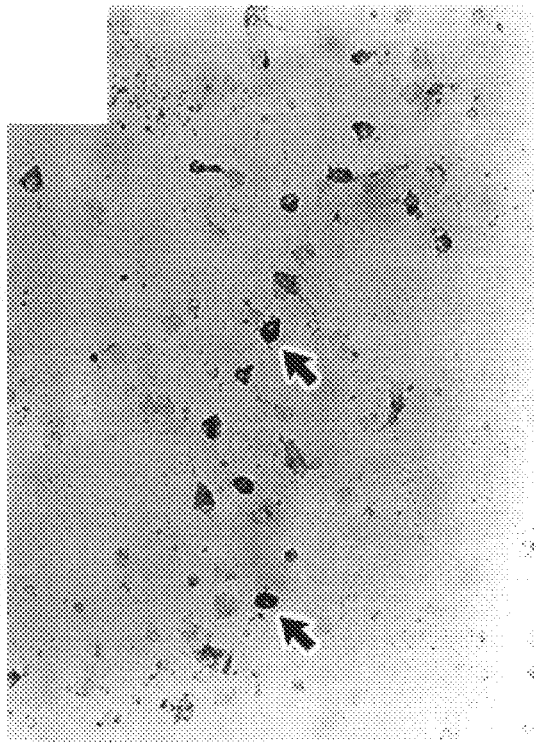
Figure 8C:
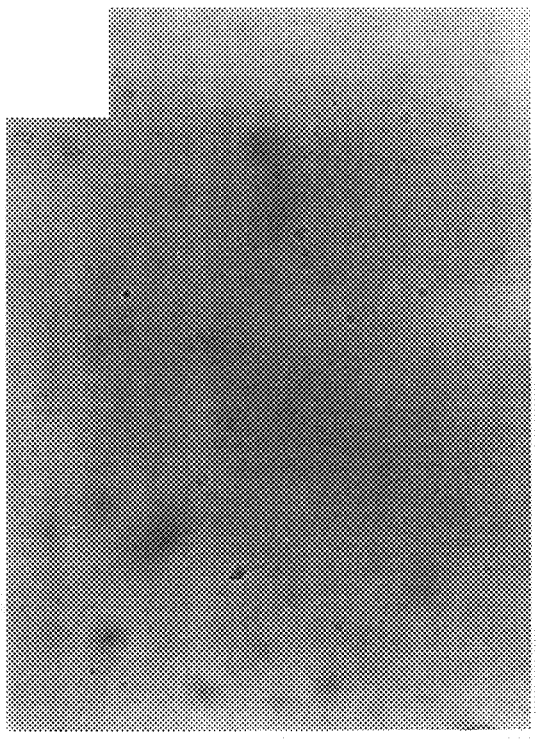
Figure 8D:
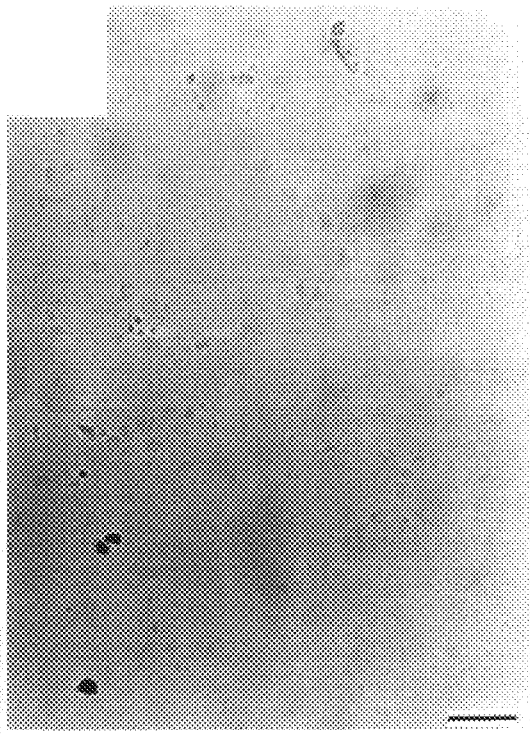

Immunocytochemical evidence of neuronal COX-2 expression/regulation in response to glutamate ini vitro. Primary cultures of rat hippocampal neurons were exposed to glutamate in vitro. At baseline, constitutive COX-2 expression was demonstrated by immunocytochemistry (FIG. 8B). Twelve hours after exposure to glutamate, an increase in COX-2 immunoreactivity was observed which coincided with marked reduction in the number of neurons (FIG. 8D).

COX-2 expression in human epilepsy. Increased expression of COX-2 mRNA was detected by ISH in a biopsy of human brain at epileptic foci (FIG. 19A and B).

7. EXAMPLE: NIMESULIDE SUPPRESSES CYTOKINE AND NITRITE PRODUCTION IN MICROGLIA CULTURES

Figure 9A:
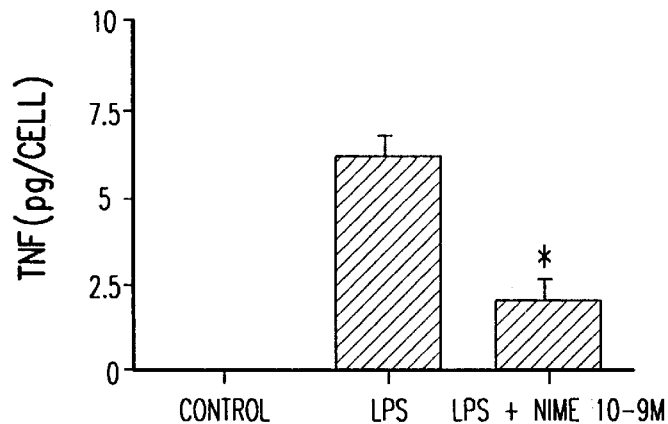
Figure 9B:
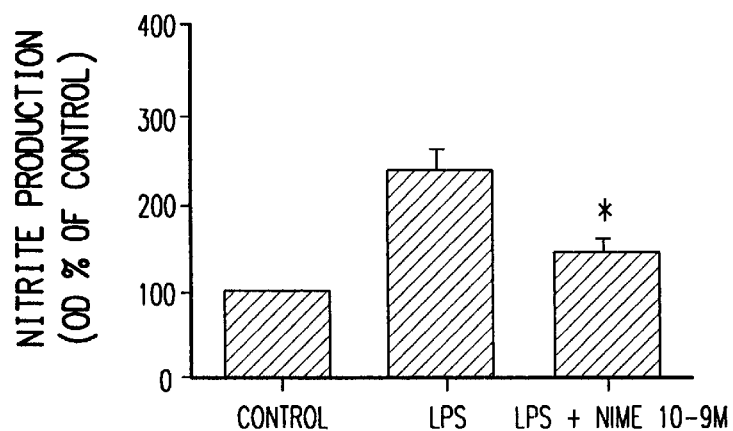
Figure 9C:
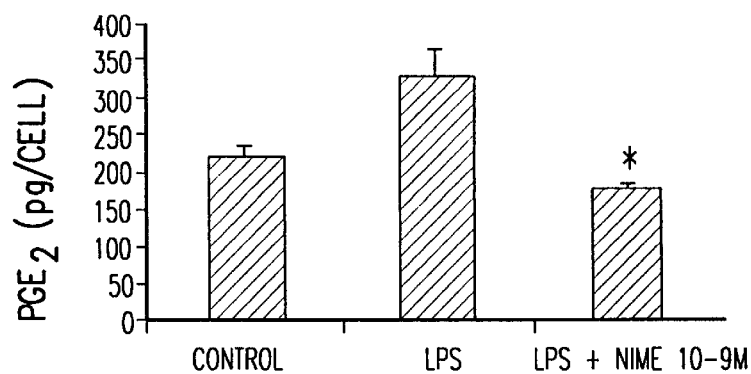
Figure 10A:
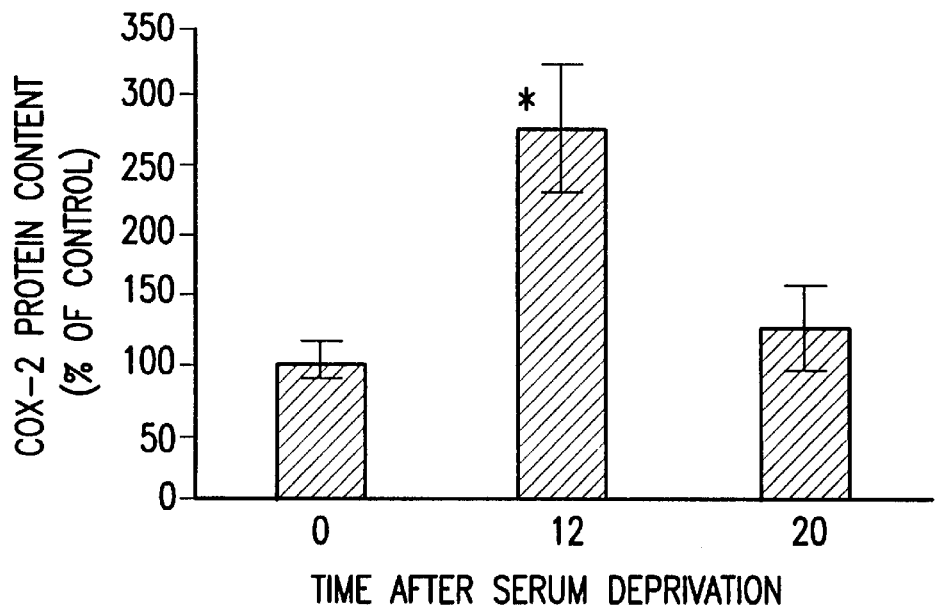
Figure 10C:
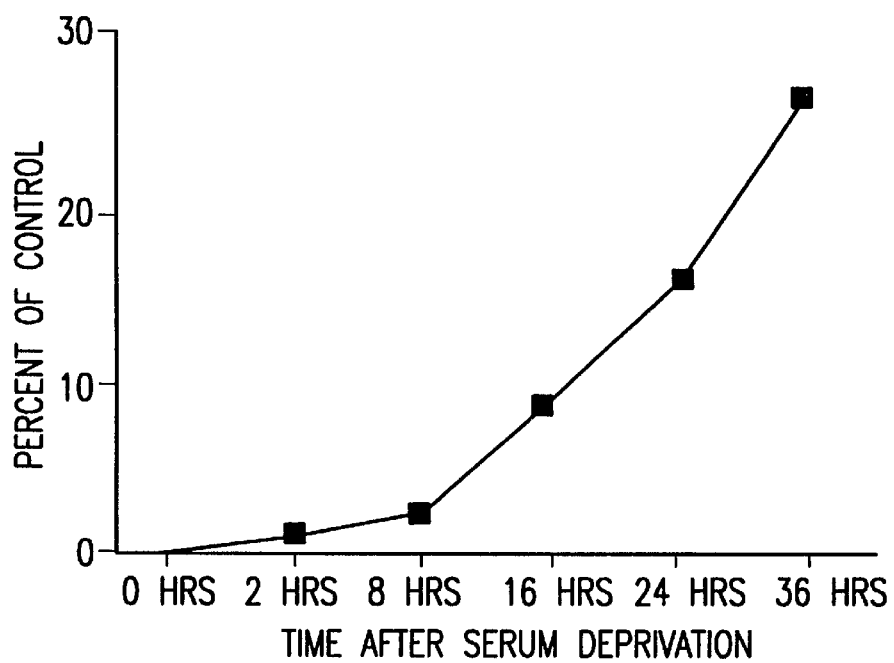
Figure 10B:
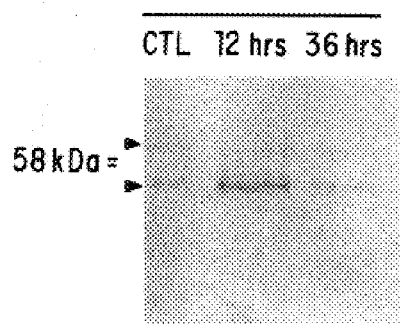
Figure 10D:
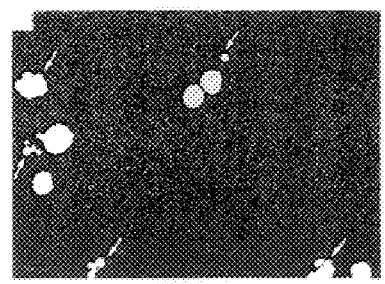
Figure 10E:
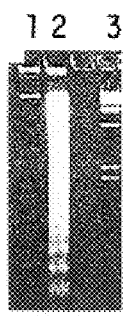

In experiments conducted in vitro, nimesulide at low concentration (1 nanomolar) was found to be effective in the suppression of endotoxin-mediated induction of tumor necrosis factor ("TNF") production by immortalized brain-derived microglia (BV-2) and astrocytes (FIG. 9A). In parallel, nimesulide was equally effective in blocking nitrite production (Griess reaction; FIG. 9B). This latter observation is particularly relevant in view of evidence showing that blockade of neuronal nitric oxide ("NO")-synthase protects against glutamate neurotoxicity. Nimesulide was also found to be effective in blocking endotoxin-mediated induction of prostaglandin $PGE_2$) in brain-derived microglia (FIG. 9C).

8. EXAMPLE: COX-2 EXPRESSION IN APOPTOTIC CELLS

The regulation of COX-2 expression was studied using an established in vitro model of apoptosis. Specifically, the regulation of COX-2 was studied in P19 embryonic carcinoma cells during responses to serum deprivation. Under such conditions, the P19 cells underwent apoptotic cell death, showing characteristic DNA fragmentation and nuclear morphology. As shown in FIG. 10, using this system, coincidental onset of apoptosis and elevation of COX-2 expression was observed.

Figure 11A:
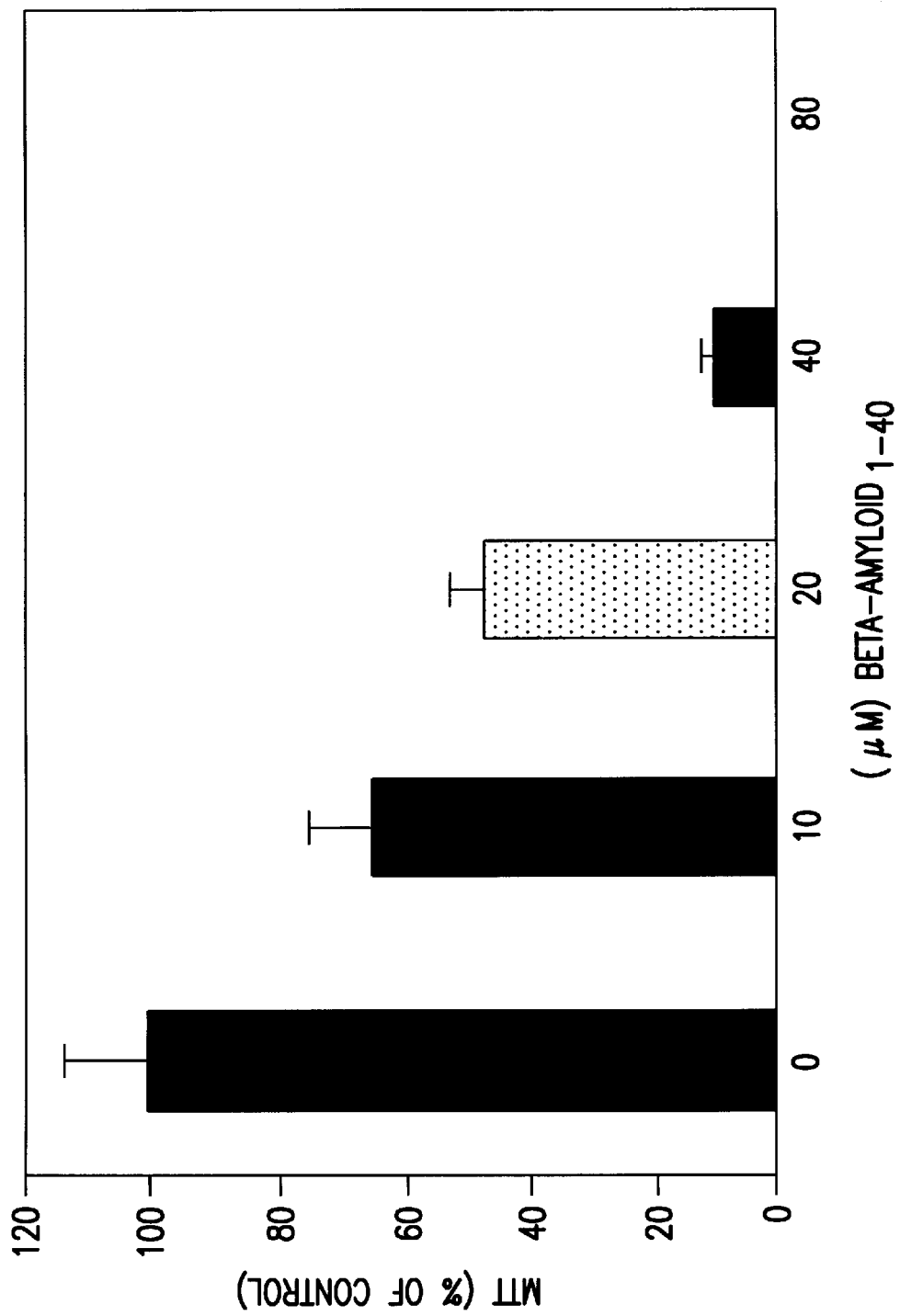
Figure 11B:
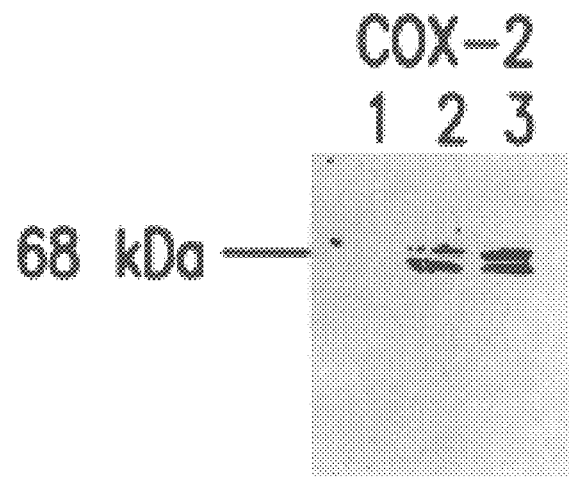
Figure 11C:
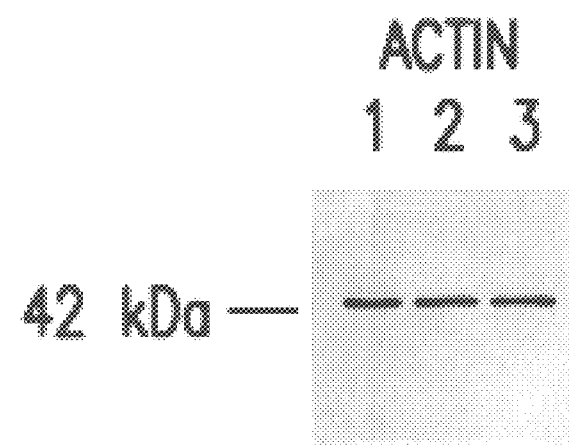
Figure 11D:
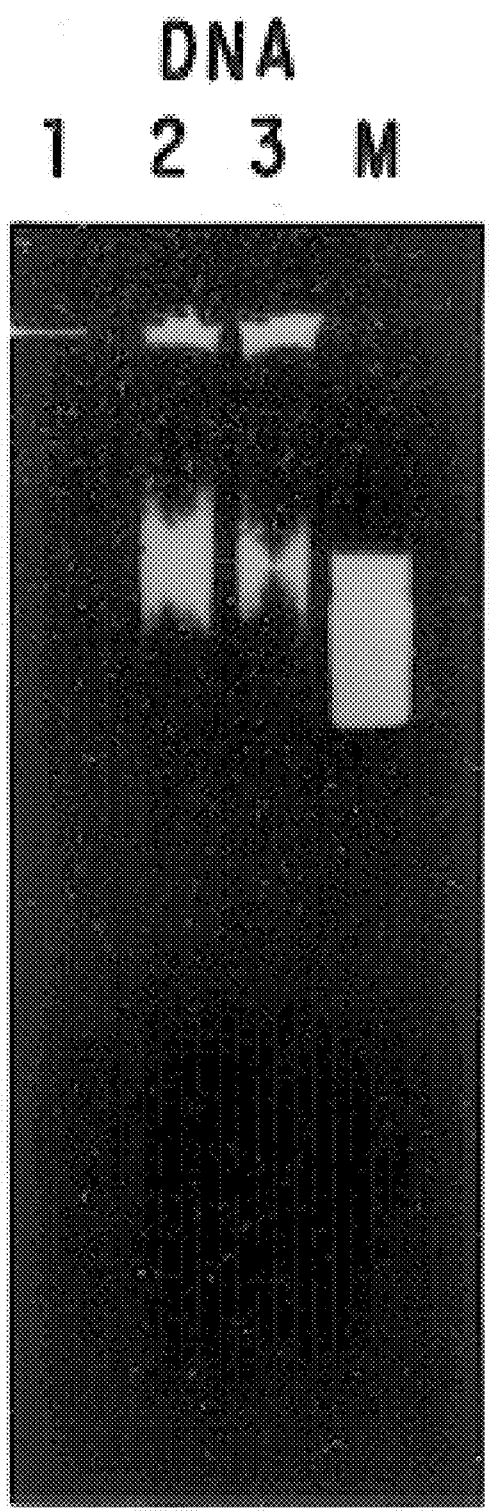

These studies were extended to the human neuronal cell line SH-SY5Y. β-amyloid has been demonstrated to play a role in inducing neurodegencration in SH-SY5Y cells (Oda et al., 1995, Alzhcimers Res. 1:29–34). As shown in FIG. 11A, the toxicity of β-amyloid ("Aβ1-40") was demonstrated in SH-SY5Y cells using the MTT assay (Id.) as a measure of oxidative stress. FIG. 11B shows that 10 and 20 μM Aβ1-40 were found to induce COX-2 expression; this occurred in parallel to DNA laddering (FIG. 11D), an index of apoptosis. As shown in FIG. 11C, actin expression did not increase. FIG. 12 shows that nimesulide at $10^{-6}$ and $10^{-9}$ molar was able to block Aβ1-40 toxicity, as assessed by the MTT assay.

9. EXAMPLE: COX-2 EXPRESSION IN ALZHEIMER'S DISEASE

The expression of COX-2 in normal human brains and in brains of Alzheimer's Disease ("AD") patients was studied. Immunocytochemical data indicates that COX-2 expression is localized to cells with neuronal morphology in human brain; no apparent localization of COX-2 immunostaining in cells with glial morphology was found in any region examined. These results tend to suggest a role for COX-2 in a non-inflammatory function. While the immunocytochemical signal for COX-2 was at the limit of detection in temporal cortex of neurological control cases, COX-2 showed elevation in AD brain (FIG. 13A, 13B and 15A). The selective induction of COX-2 immunoreactivity in grey matter is consistent with the findings showing neuronal induction of COX-2 in rat brain during responses to lesions leading to neuronal death (see Section 6).

Figure 14A:
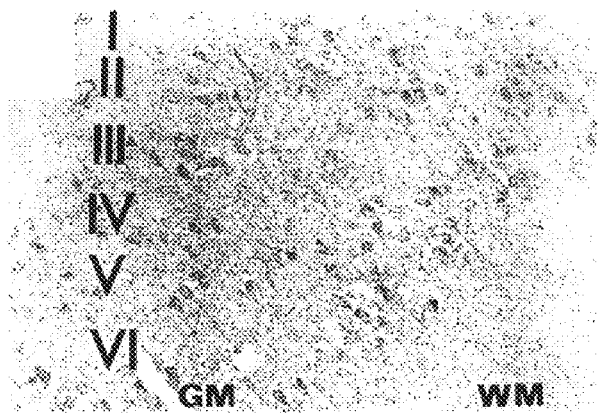
Figure 14C:
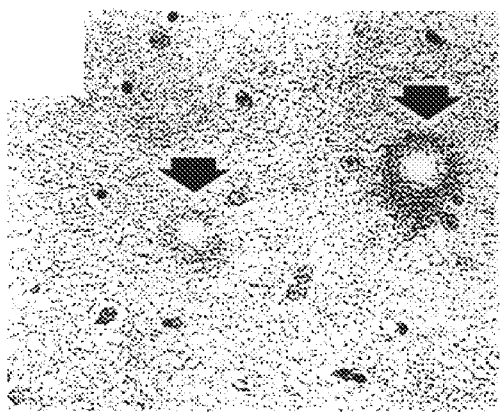
Figure 14B:
Figure 14D:
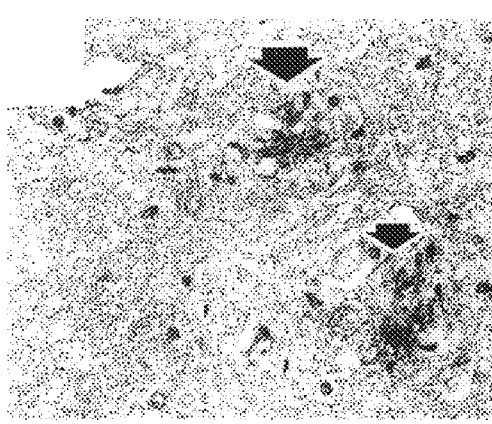

The cellular immunodistribution of COX-2 in AD brain was also explored. It was observed that neuronal COX-2 is not only localized to the perikarya (FIG. 14A, but is found in neuronal projections as well (FIG. 14B). Moreover, intense immunostaining was also found around vessels (FIG. 14C) and in AD plaques identified by Aβ immunostaining on adjacent tissue sections of the hippocampal formation (FIG. 14D). These findings suggest a role for COX-2 in mechanisms of neuronal death or survival.

Studies were perfonned to quantify COX-2 expression in brains of AD and age-matched controls. We used quantitative dot-blot analysis and chemiluminescence detection. Western analysis was used for qualitative assessment. A greater than 2-fold elevation of COX-2 content was found in hippocampal homogenates of AD brains compared to neurological age-matched controls (FIG. 15).

Because of the immunocytochemical evidence showing COX-2 immunoreactivity in AD plaques, levels of COX-2 and total Aβ in AD cases were compared. A direct correlation was found (FIG. 16).

Figure 17B:
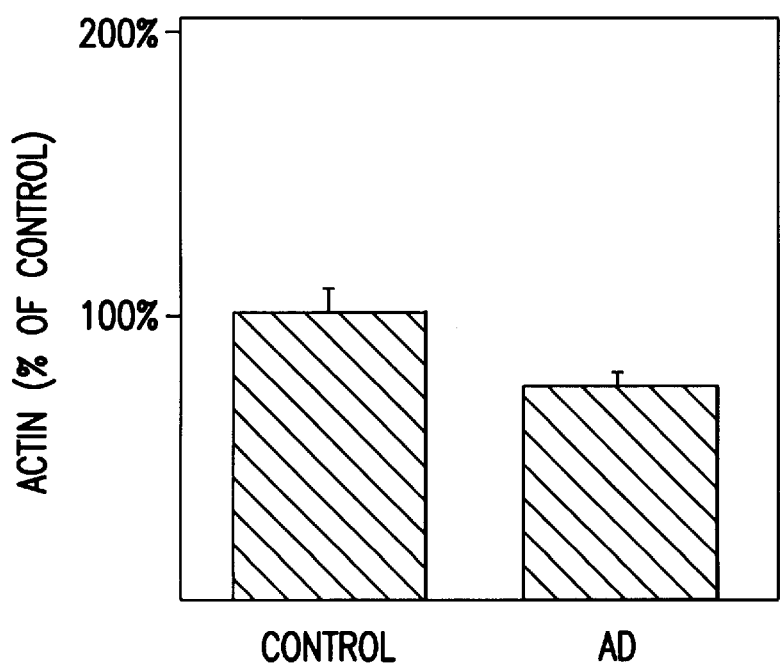

When COX-2 expression in the frontal cortex and hippocampus of Alzheimer's brains was studied, it was found that there was more than three-fold (FIGS. 17A and 17B) elevation of mean COX-2 levels in the frontal cortex of Alzheimer's brains compared to neurological controls, confirming COX-2 immunocytochemical data obtained using temporal cortex of Alzheimer's patients.

11. EXAMPLE: COX-2 EXPRESSION IN AMYOTROPHIC LATERAL SCLEROSIS

In situ hybridization has demonstrated increased COX-2 mRNA in the anterior horn cells of spinal cords of patients suffering from amyotrophic lateral sclerosis ("ACS"); FIG. 18).

Various publications are cited herein, the contents of which are hereby incorporated in their entireties.

What is claimed is:

1. A method of preventing non-inflammatory neuronal cell death in a patient suffering from a neurodegenerative condition comprising administering, to the subject, an effective amount of nimesulide.

2. The method of claim 1, where the neurodegenerative condition is Alzheimer's Disease.

3. A method of preventing neuronal cell death in a patient suffering from amyotrophic lateral sclerosis comprising administering, to the subject, an effective amount of nimesulide.

4. A method of preventing neuronal cell death in a patient suffering from a neurodegenerative condition is caused by chronic epilepsy comprising administering, to the subject, an effective amount of nimesulide.

5. The method of claim 1, wherein neurons affected by the neurodegenerative condition are exposed to a concentration of nimesulide of at least one micromolar.

6. The method of claim 2, wherein neurons affected by the neurodegenerative condition are exposed to a concentration of nimesulide of at least one micromolar.

7. The method of claim 3, wherein neurons affected by the neurodegenerative condition are exposed to a concentration of nimesulide of at least one micromolar.

8. The method of claim 4, wherein neurons affected by the neurodegenerative condition are exposed to a concentration of nimesulide of at least one micromolar.

9. A method of treating Alzheimer's disease comprising administering, to a subject in need of such treatment, a neuroprotective amount of nimesulide which results in exposure of the affected neurons to a local concentration of nimesulide of one micromolar or a lower concentration that inhibits neuronal cell death by at least 20 percent.

* * * * *

UNITED STATES PATENT AND TRADEMARK OFFICE
CERTIFICATE OF CORRECTION

PATENT NO. : 5,985,930
DATED : November 16, 1999
INVENTOR(S) : Pasinetti et al.

It is certified that error appears in the above-identified patent and that said Letters Patent is hereby corrected as shown below:

Title page,
Item [76], Inventors:
"Paul S. Aisen, 26 Broadmoor Rd., Scarsdale, N.Y. 10583" should read -- Paul S. Aisen, 12308 Piney Glen Lane, Potomac, MD 20854 --, so that Item [76] reads:
-- Giulio M. Pasinetti, 134 E. 93rd St., New York, NY 10028; Paul S. Aisen, 12308 Piney Glen Lane, Potomac, MD 20854 --.
Item [73], Assignee: -- Mount Sinai School of Medicine of New York University, New York (NY) -- should be inserted.

Signed and Sealed this

Seventh Day of September, 2004

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 5,985,930 |
| APPLICATION NO. | : 08/831402 |
| DATED | : November 16, 1999 |
| INVENTOR(S) | : Giulio M. Pasinetti and Paul S. Aisen |

It is certified that error appears in the above-identified patent and that said Letters Patent is hereby corrected as shown below:

Please insert, before Col. 1, line 7 ("INTRODUCTION"), the following paragraph:

-- This invention was made with government support under NIA grant numbers AG 13799, AG 14239, and AG 05138 awarded by the National Institutes on Aging. The United States Government has certain rights in the invention. --

Signed and Sealed this

Twenty-seventh Day of October, 2009

David J. Kappos
*Director of the United States Patent and Trademark Office*